United States Patent [19]

Myers

[11] Patent Number: 5,108,179

[45] Date of Patent: Apr. 28, 1992

[54] SYSTEM AND METHOD FOR DETERMINING CHANGES IN FLUORESCENCE OF STAINED NUCLEIC ACID IN ELECTROPHORETICALLY SEPARATED BANDS

[76] Inventor: Stephen A. Myers, 25 Nimitz Pl., Old Greenwich, Conn. 06870

[21] Appl. No.: 391,481

[22] Filed: Aug. 9, 1989

[51] Int. Cl.⁵ .............................................. Q01J 3/10
[52] U.S. Cl. .................................. 356/344; 356/318; 356/417; 250/459.1
[58] Field of Search ............... 356/317, 318, 417, 344; 250/458.1, 459.1, 461.1; 204/182.8, 299 R

[56] References Cited

U.S. PATENT DOCUMENTS

| | | |
|---|---|---|
| 4,758,727 | 7/1988 | Tomei et al. ...................... 250/458.1 |
| 4,820,398 | 4/1989 | Yamamoto ....................... 204/182.8 |
| 4,833,332 | 5/1989 | Robertson et al. ................. 356/417 |
| 4,881,812 | 11/1989 | Ohkubo et al. .................... 356/344 |
| 4,890,247 | 12/1989 | Sarrine et al. ..................... 204/182.8 |
| 4,960,999 | 10/1990 | McKean et al. ................... 250/458.1 |

Primary Examiner—Richard A. Rosenberger
Attorney, Agent, or Firm—Edward S. Irons; Thomas S. Hahn

[57] ABSTRACT

The use of continuous wave (CW) laser excitation to measure small differences in the fluorescence of bands of fluorophore stained nucleic acid fragments present in gels is described.

20 Claims, 33 Drawing Sheets

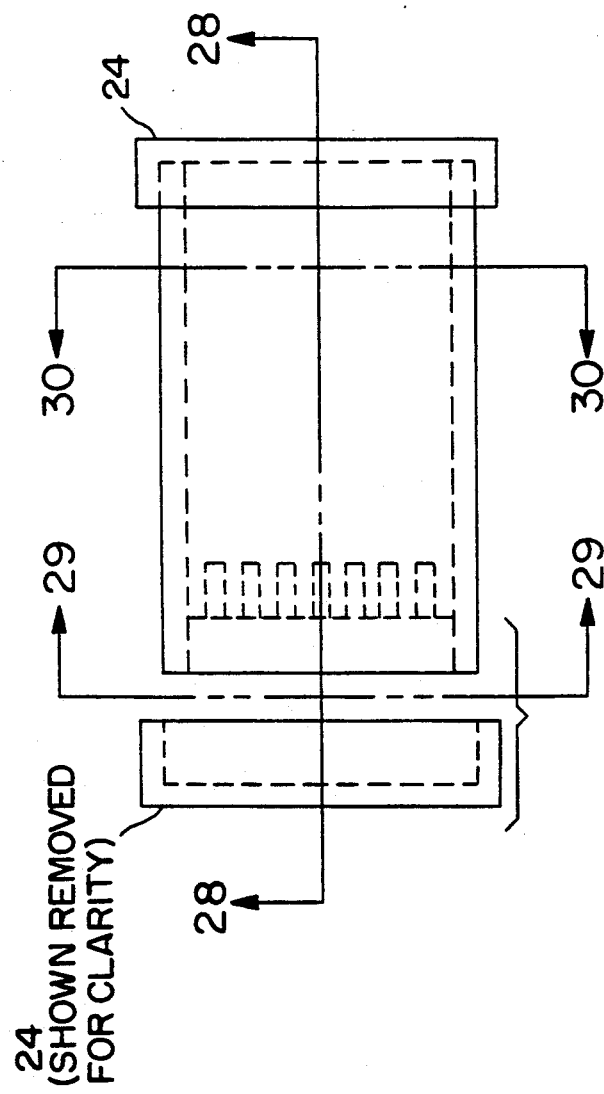
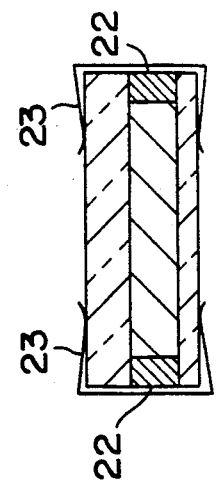
FIG. 27
FIG. 28
FIG. 29
FIG. 30

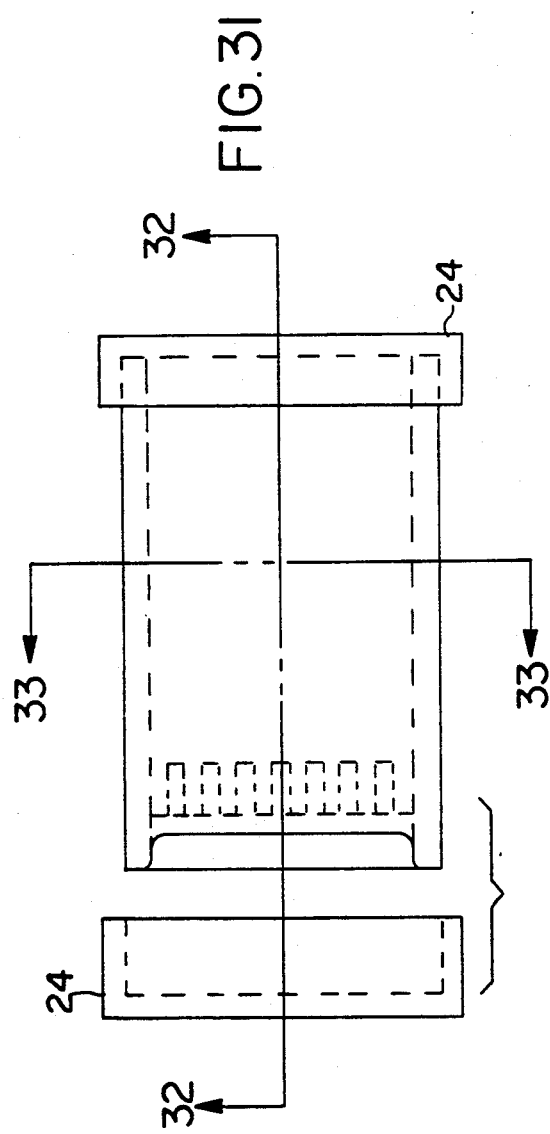
FIG.31
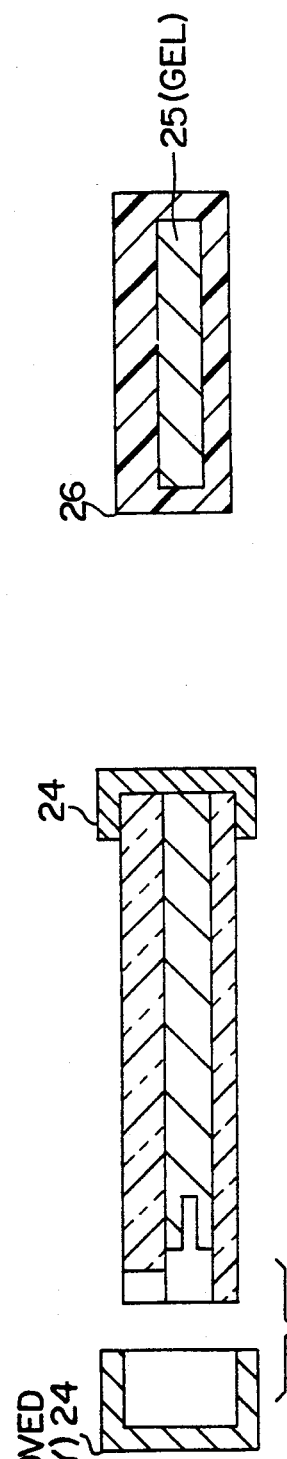
FIG.33
FIG.32

SYSTEM AND METHOD FOR DETERMINING CHANGES IN FLUORESCENCE OF STAINED NUCLEIC ACID IN ELECTROPHORETICALLY SEPARATED BANDS

The invention pertains to the use of continuous wave (CW) laser excitation to measure small differences in the fluorescence of bands of fluorophore stained nucleic acid fragments present in gels.

BACKGROUND OF THE INVENTION

Gel electrophoresis is an important technique widely used for separating biological molecules by molecular weight. At present, restriction fragment analysis of nucleic acid using gel electrophoresis is predominantly used as (1) a qualitative technique, e.g., for assessing the success of a particular cloning step in terms of the presence or absence of specific fragments, base pair sequencing, determining the possible presence of impurities, etc., or (2) as a quantitative means of measuring the molecular weight (molecular length) of the separated fragments in terms of their dispersed position. Much less common has been the additional measurement of the mass of separated nucleic acid which can be determined from the intensity of the fluorescence of the stained sample.

The principal method now employed to detect the distribution of DNA or RNA strands separated by gel electrophoresis involves use of a fluorescent dye, e.g., ethidium bromide. Under the proper conditions the sample mass is directly proportional to the fluorescence signal (1, 2). Present methods of measuring the mass distribution in terms of fluorescence (visual estimation, photography/scanning densitometry, electronic imaging) are labor intensive, slow or have one or more of the following drawbacks: limited accuracy, insufficient sensitivity, and restricted dynamic range. These drawbacks have restricted the wider use of mass distribution measurements.

After separation the most common procedure is to expose the stained gel to mid-ultraviolet illumination centered at 310 nm provided by a transilluminator containing one or more low wattage, UV emitting lamps. The resulting sample fluorescence with peak emission in the orange at 590 nm is observed visually or photographed.

The simplest means for estimating the mass of the separated fragments is to visually compare the brightness of the fluorescence of the separated sample bands to that from a reference standard of known sample mass added to an adjacent lane of the gel which separates into a simple pattern of fragments whose individual mass can be closely estimated. The method is inaccurate because the observer cannot easily correct for the differing fluorescence intensities from two samples of equal mass but spread out over different areas.

Densitometer tracings of the photographic negative of the fluorescent band pattern are frequently employed to accurately determine the distances of migration of polydisperse samples. This procedure has important limitations when used to measure the fluorescence intensity to determine the mass of dispersed DNA in each band. The darkening of the photographic negative is linearly proportional to the logarithm of the exposure over a limited exposure range between one and two orders of magnitude. Within this range the fluorescence intensity, I, may be expressed as:

$$I \alpha 10^D / \gamma.$$

where D is the optical density (in the range above threshold for linearity) measured by the densitometer, and $\gamma$ is the contrast index or slope of the linear portion of optical density plotted against log exposure. Since the fluorescence intensity is indirectly derived from a densitometer measurement, it is subject to inaccuracies and noise involved in the measurement of the optical density.

The contrast index of the film can be markedly affected by the development time, and to a lesser extent by the development temperature, storage conditions, and the exposure time (reciprocity failure). The stringent controls which are required to prevent unacceptable variations are inconvenient to maintain in routine analysis. Instead, suitable DNA standards which span the mass range of interest are introduced on every gel to provide a calibration curve. The camera exposure time must be chosen carefully so that the range of exposures closely matches the linear portion of the film characteristic curve to prevent unacceptable flattening of the calibration curve at its ends. This procedure is labor intensive and limits the number of samples which can be prepared and analyzed.

The densitometer measurement time can become unacceptably long. Often the DNA is not distributed uniformly across the lane and an accurate measurement of fluorescence requires sampling at more points than are normally required to measure the lane position. The densitometer sampling spot size must be small compared to spatial variation in density or error will result, further increasing the measurement time. Additional points must also be sampled adjacent to each lane to permit accurately correcting for the baseline fluorescence contributed by the residual free dye which remains after destaining.

The accuracy of the method is also affected by the uniformity of the UV illumination, since the fluorescence is directly proportional to the intensity of the exciting light. Variation across the field-of-view can be 10% or greater using commercial transilluminators. There is also considerable drift in intensity with warmup time. The sensitivity is limited by a high level of background light from several sources unrelated to the stained gel (3).

Electronic imagining of the gel has been employed which measures the fluorescence intensity directly and greatly reduces the measurement time (4). The method has the drawbacks of limited dynamic range, and difficulties in correcting accurately for variation in the illumination over the field-of-view and for pixel-to-pixel sensitivity variation. As with photography, highly accurate measurements of mass are hindered by geometric field distortion, vignetting, and loss of resolution unless the field angle is severely limited, particularly for thick sample gels. Reduced signal-to-noise ratio at low light levels has led to little improvement in sensitivity over the photographic technique.

CW lasers have been employed as excitation sources in tube gels (5) and most recently with slab gels in various automated DNA sequencers which detect separated DNA fragments labelled with fluorophores specific to the base pair terminating the fragment (6-11). Large improvement in sensitivities has been reported for polyacrylamide gels and dyes which differ from ethidium bromide. However, there are no reports for the use of such instruments for measurement of nucleic acid mass using ethidium bromide in either polyacrylamide or agarose gels and the descriptions of their design do not include the unique performance requirements for that application.

SUMMARY OF THE INVENTION

This invention provides, among other things, an instrument and a method for the direct accurate measurement, as a function of the intensity of stimulated fluorescence, of the mass of fluorophore stained nucleic acid fragments present in electrophoretically separated bands in a gel.

In contrast to the prior art, both the accuracy and sensitivity of the measurement are enhanced. Enhanced performance stems from (1) instrumental improvements in the way the fluorescence is stimulated, collected and detected, (2) improvements in the preparation of the gel which impart greater uniformity to the stained background, and (3) improved data processing which more accurately corrects for residual fluorescence variation in the background.

The ability provided by the invention to accurately determine the mass of nucleic acid fragments is of manifest practical importance (12, 13). The ability to detect small changes in fluorescence accommodates the use of fluorophore tagged probes as a substitute for autoradiography (14).

The system of the invention also permits achievement of performance advantages associated with capillary electrophoresis, i.e., the ability to handle very small sample sizes, elimination of gel preparation and destaining, more rapid separation and increased resolution.

As compared with capillary electrophoresis, which must process one sample at a time, this invention permits simultaneous processing of many samples, thus providing an increase in sample throughput.

BRIEF DESCRIPTION OF THE DRAWINGS

FIG. 27 is a view of a gel cassette contemplated by the invention.

FIG. 28 is a section of the gel cassette taken on the line 28—28 of FIG. 27.

FIG. 29 is a view of the gel cassette taken on the line 29—29 of FIG. 27.

FIG. 30 is a section of the gel cassette taken on the line 30—30 of FIG. 27.

FIG. 31 is a view of an injected molded gel cassette.

FIG. 32 is a sectional view taken on the line 32—32 of the cassette shown in FIG. 31.

FIG. 33 is a sectional view taken on the line 33—33 of the cassette shown in FIG. 31.

SYSTEM DESIGN

Figure 1:
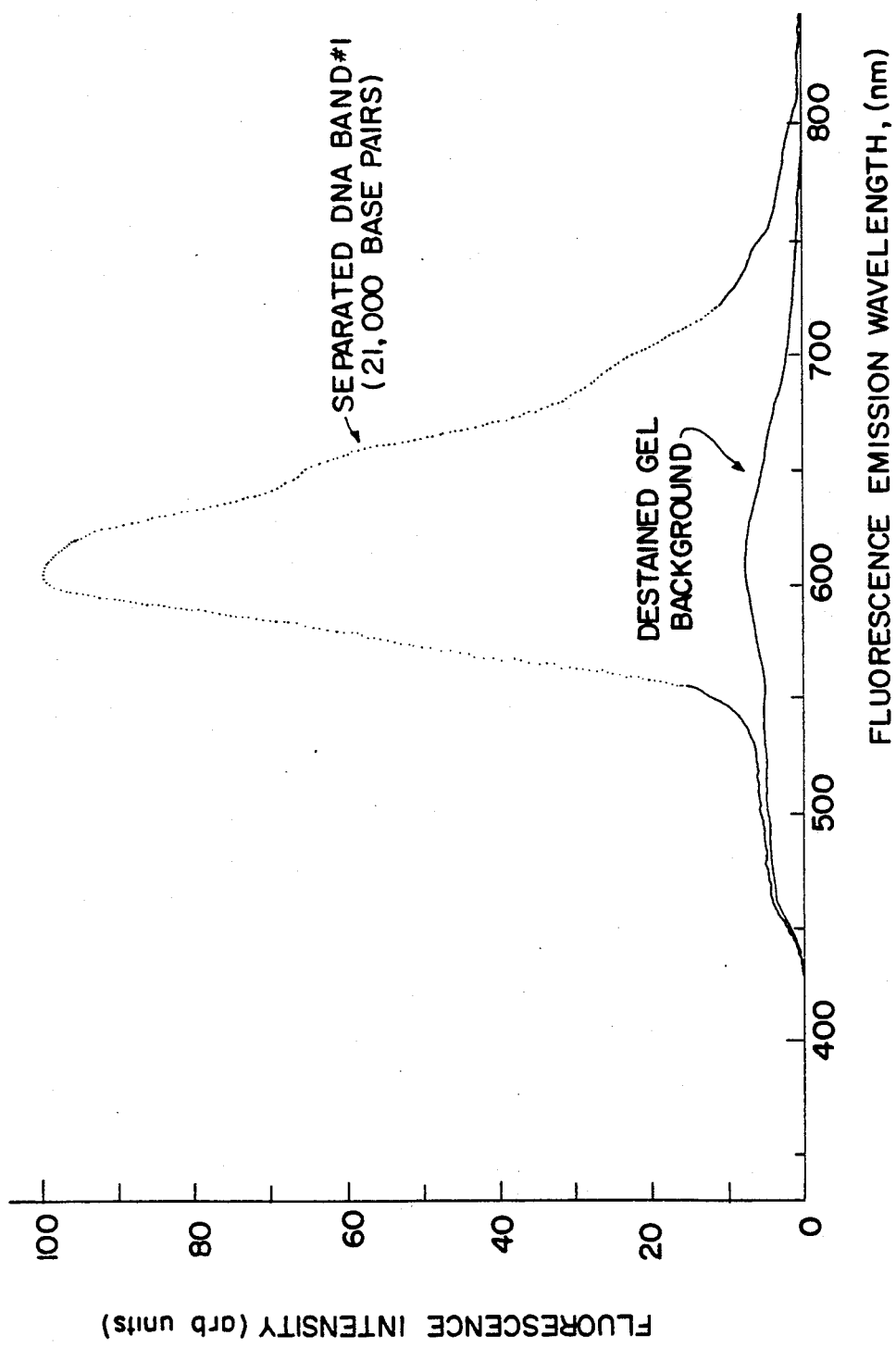
FIG. 1 is a curve which plots ethidium bromide stained DNA sample fluorescence against emission wavelength.

Early experimental work (3) led to the conclusions that (1) the measurement of nucleic acid separated by gel electrophoresis could be transformed into a sensitive, highly accurate quantitative technique, and (2) fluorescent light levels from the stained sample can be great enough to permit very rapid scanning of a gel sample at high resolution with laser light sources of moderate power without shot noise in the detected signal becoming the limiting source of noise. The measurement time can be acceptably short without sacrificing performance.

To fully realize the substantial gain in performance possible, this invention provides an improved instrumental design which (1) meets several optical performance standards in order to make highly accurate measurements of separated nucleic acid in the gel medium, (2) employs visible rather than UV excitation despite lower fluorescence efficiency, and which (3) overcomes the large variation in the background fluorescence signal which is the major obstacle to achieving a more accurate measurement of mass and to improving the detection limit.

Optical Performance Criteria Imposed by Gel Thickness

Inspection of sectioned gels indicates that separated DNA bands can be found at any point within the thickness of the gel. A general purpose instrument must accept gels which range in thickness from less than 1.0 mm to over 5.0 mm. In order to preserve accuracy of the measurement of mass, the fluorescence measurement should be largely or completely insensitive to possible variation in the distribution of the sample within the gel thickness. Normally when the light stimulating fluorescence is spread out over a broad sample area, the f/no. of the fluorescence collection optics determines the resolution which can be obtained for a given sample thickness.

Experimental measurement of the brightness of the sample fluorescence (3) and estimation of the signal-to-noise (S/N) performance for an optical system which employs high f/no optics to maintain adequate resolution in a moderately thick agarose gel (3.0 mm) indicates that low fluorescence light collection efficiency is an important factor limiting the S/N. To achieve adequate S/N, the required sample measurement time becomes unattractively long. Use of CW laser illumination overcomes this problem by providing a beam with adequate power that can also be focused into a spot of small diameter, e.g., from about the diameter of the laser beam to about 0.005 mm. The resolution is then set by the narrow diameter of the laser beam instead of the f/no of the optics. The use of fast, low f/no, e.g., less than f/1, optics becomes possible in the presence of an optically thick sample leading to an increased fluorescence signal, improved S/N, and much shorter measurement times.

A second desideratum for accurate mass measurement is that the diameter of the incident beam remain constant as it passes through the gel. Otherwise the intensity of the fluorescence may vary with beam diameter for a given element of sample mass depending upon its position within the gel thickness. The coherence of the laser light (preferably emitted in the lowest order 0-0 transverse mode) permits easily maintaining a nearly constant cross-sectional area of the beam over even the thickest gels (>10.0 mm).

A third criterion is that the light throughput efficiency of the optical system which images the sample fluorescence onto the detector preferably remain nearly constant over the gel thickness.

Other Optical Considerations (1) The sample fluorescence signal should be independent of the power density variation over the cross sectional area of the light beam stimulating fluorescence. The fluorescence signal is proportional to the convolution of the beam profile with the sample density variation. This invariance criterion is met if either factor is unvarying over the range of variation of the other, i.e, uniform incident light beam over a varying sample density or a nonuniform beam over a constant sample density. The latter condition can be closely approached with a laser beam which can be focused into a beam diameter of less than about 10 $\mu$m if required, over which the sample density is essentially constant.

(2) Means to accurately correct for fluorescence contribution of the stained gel background should be provided. The background contribution is inferred from measurements made adjacent to the sample band, either between discrete bands within the separation lane, or from off-lane positions known to be free of separated sample. Both sufficient resolving power and an adequate number of measurements is required to sample the spatial variation of the fluorescence signal with minimal distortion. The angle of incidence which the laser beam makes with respect to the direction perpendicular to the surface of the gel should be as small as possible, consistent with the gel thickness and desired spatial resolution, and the need to suppress interference fringing, for example, for agarose gels 3°, 3.0 mm thick, 10° for 0.4 mm thick. Otherwise the horizontal displacement of the beam as it passes through the gel can reduce the effective resolution.

(3) The sample should not change over the measurement time in a way which affects its fluorescent response, e.g., change caused by evaporation.

Visible Excitation is Preferable to Ultraviolet

Figure 2:
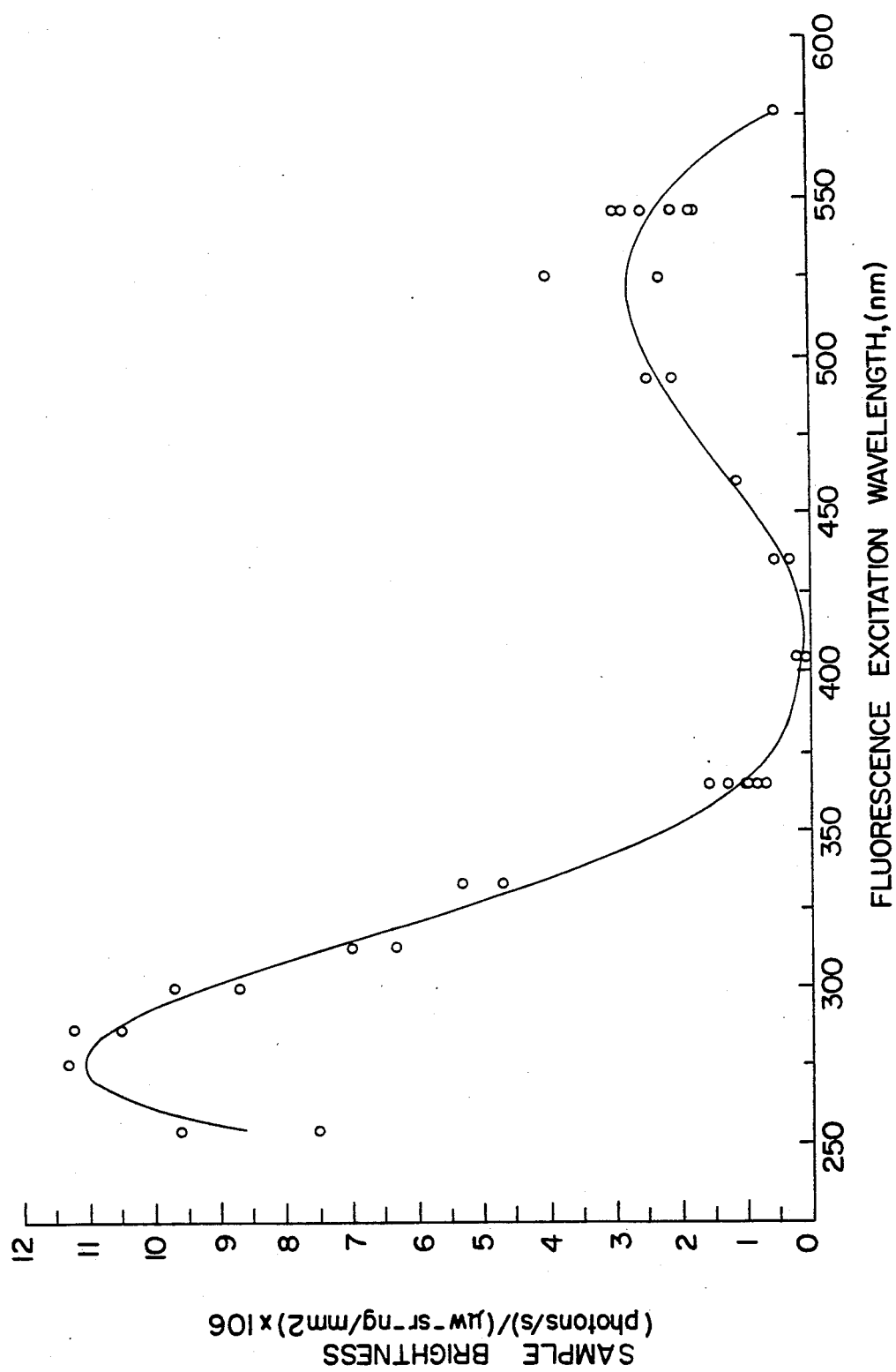
FIG. 2 is a curve which plots sample brightness of the FIG. 1 sample versus excitation wavelength.

Sample fluorescence versus wavelength is shown in FIG. 1 (3). FIG. 2 illustrates sample brightness, (summing the fluorescence intensity from 550 nm to 750 nm from spectra such as FIG. 1), versus excitation wavelength. Fluorescence excitation is possible either in the UV from approximately 250 nm to 350 nm, or in the visible from approximately 470 nm to 570 nm. The higher fluorescence efficiency in the UV is one reason that excitation at 300 nm is more commonly employed.

Several experimental observations support the conclusion that visible excitation is preferable to UV despite the lower fluorescence efficiency.

(1) Appreciable gel thickness also imposes the requirement that both the incident light and the sample fluorescence passing through the gel should not be significantly attenuated by either absorption or scattering caused by the gel. Otherwise fluorescence intensity again depends upon position within the thickness of the gel. The attenuation of the incident beam through the combined effects of scatter and absorption is observed to be significantly greater at shorter wavelengths (3). The apparent transmission (uncorrected for surface reflection losses) through a 3.0 mm thick unstained 1.0% agarose gel has been observed to be reduced to 50% at 300 nm, but is greater than 80% at excitation wavelengths longer than 450 nm.

(2) Scattering of the incident beam from the upper surface of the gel is $1 \times 10^4$ greater than the fluorescence signal from the destained gel background. It is preferably restricted by optical filtering to at least one part in $10^6$ to adequately limit its false signal contribution. At equal incident power, the scattering is measured to be 2 times less at 546 nm than at 300 nm which aids this limiting process.

(3) The loss in sample fluorescence with increasing exposure time due to bleaching of the dye is also less at longer excitation wavelengths (3, 15). In some circumstances accuracy can be affected in repetitive scanning if the fluorescence intensity declines between scans.

(4) Photodamage to the nucleic acid sample is known to decrease with increasing wavelength (15).

Further Instrumental Considerations Favoring Visible Excitation

Figure 3:
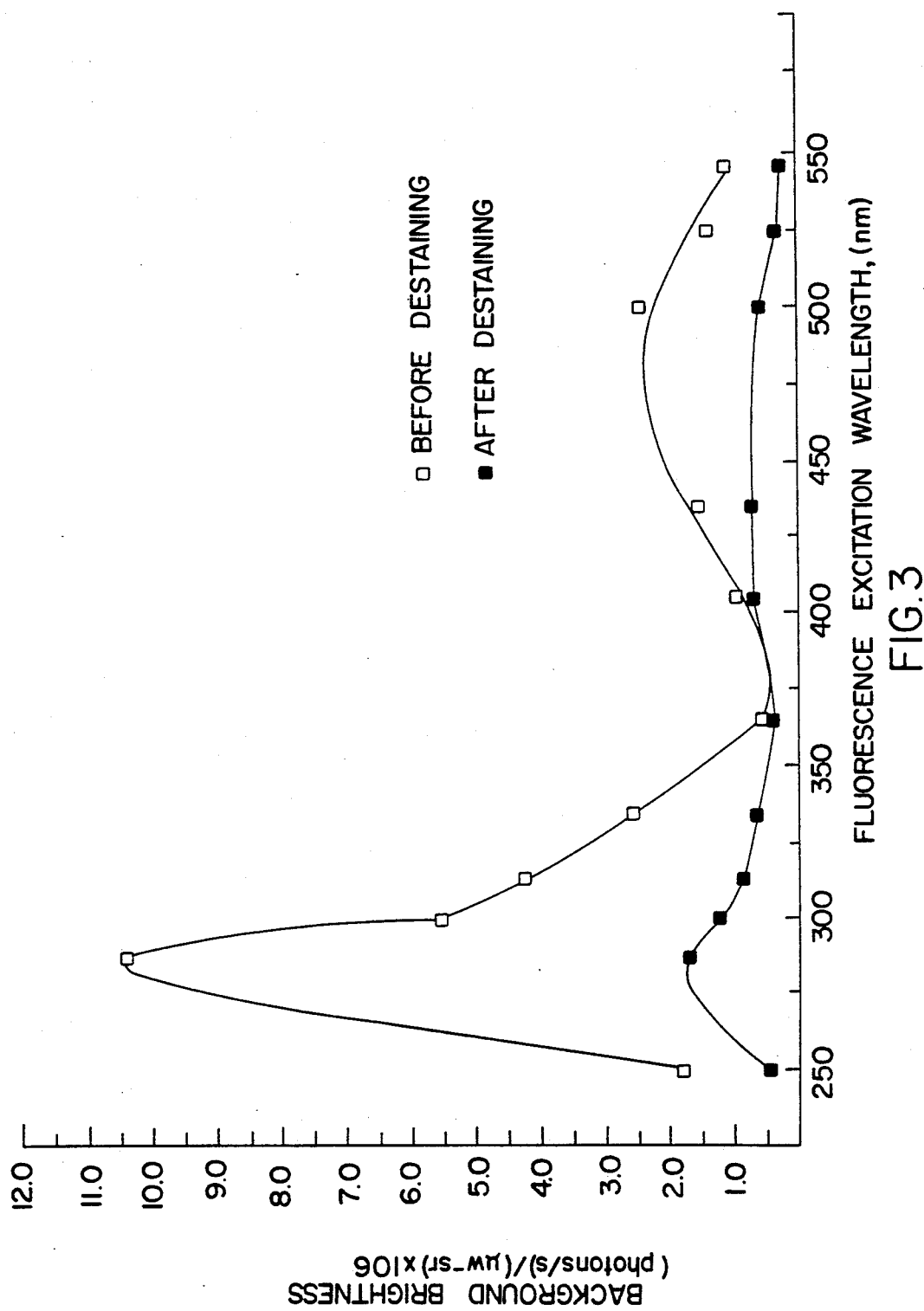
FIG. 3 is a fluorescence excitation spectrum of the gel background of the FIG. 1 sample.

The general behavior shown in FIGS. 1 and 2 has been previously described for DNA stained with ethidium bromide in water and alcohol solvents (1, 16). It has been discovered (3) that there are important differences in the detailed behavior observed in agarose gels that compensate for the nearly 4:1 greater fluorescence efficiency using UV. FIG. 3 shows that the brightness of the destained gel background is less for visible excitation than for UV excitation. The ratio of sample to background fluorescence directly affects the accuracy of background subtraction. That ratio is the same for excitation at both 300 nm and 546 nm within the experimental accuracy.

It is also a significant discovery (3) that the sample fluorescence emission shown in FIG. 1 extends 100 nm further into the red (750 nm vs 650 nm) than previously reported (1). It becomes possible to employ two highly attractive CW lasers which emit wavelengths between about 500 nm and 550 nm, (e.g., argon ion at 514.5 nm and helium neon at 543.5 nm) close to the secondary maximum shown in FIG. 2. In order to block scattered light at the excitation wavelength, a long wavelength, cut-on filter may be included in the fluorescence detection channel. The filter transition from minimum to maximum transmittance over the 550-600 nm interval necessarily attenuates part of the fluorescence signal. The loss is about 25% of the total fluorescence summed from 550 nm to 750 nm which is acceptable. (In fact, the ratio of sample to background fluorescence is somewhat higher over the limited wavelength interval of 600 nm to 750 nm than over the full 550 nm-750 nm interval.) The loss would be prohibitively great if the previously reported fluorescence cutoff at 650 nm had been observed.

The Need to limit Variation in the Fluorescence Background

The estimated background at the band position can be calculated more accurately by interpolation or extrapolation when the adjacent, sample-free background is more uniform or well-behaved. Improving the uniformity of the background therefore improves the accuracy of the measurement of band mass.

DETAILED DESCRIPTION OF THE INVENTION

Figure 4:
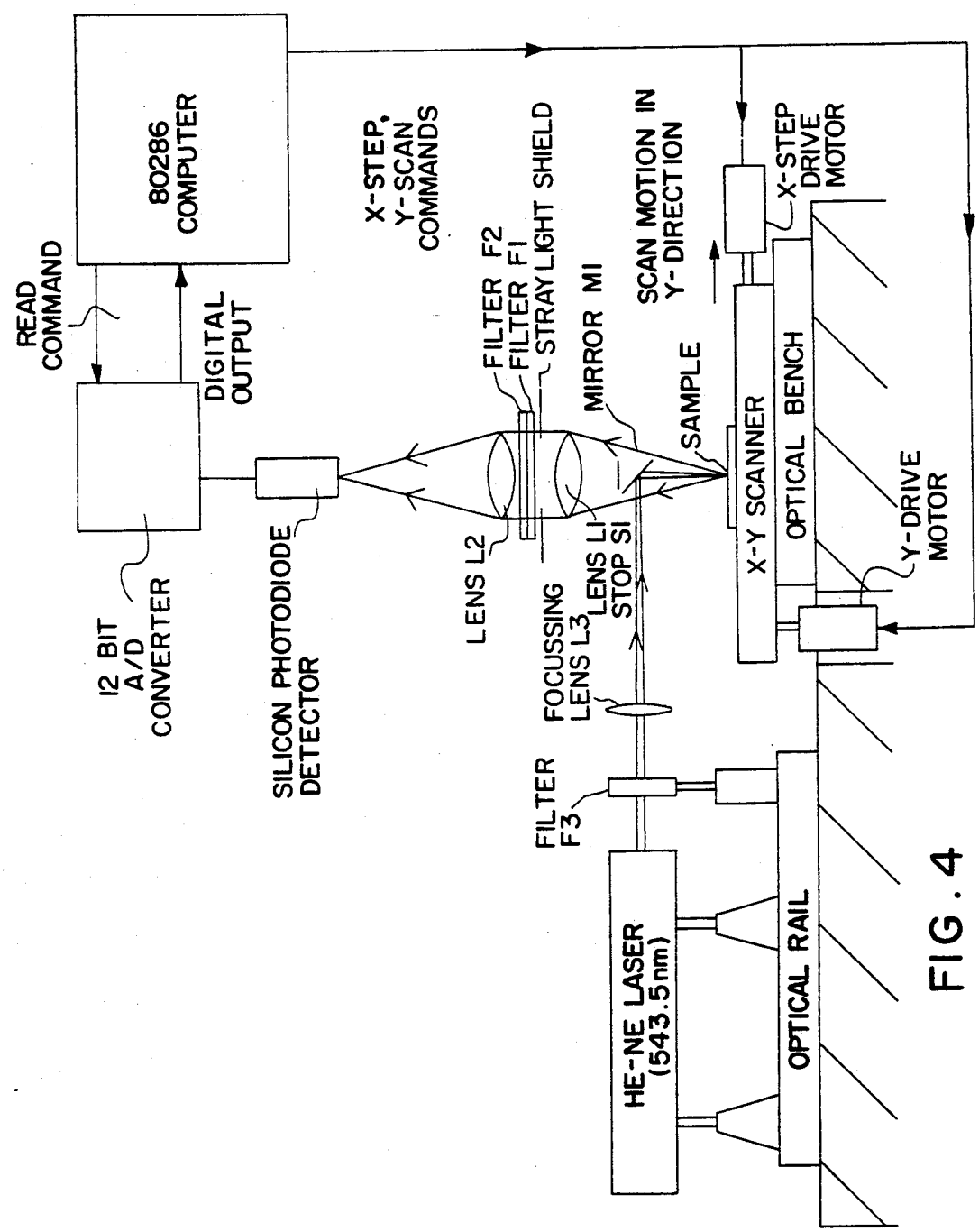
FIG. 4 is a schematic illustration of an instrument which embodies one form of the invention.

Referring to the specific embodiment of the invention shown in FIG. 4, a commercial helium-neon laser provides randomly polarized, low angular divergence, constant output in the green at 543.5 nm at a power output of 0.3 mW. Fluorescence is excited in an electrophoretically separated nucleic acid sample stained with ethidium bromide. Narrow bandpass filter F3 passes the 543.5 nm laser line but blocks the incoherent background light from the laser gas discharge. The light is focused by lens L3 into a beam with a reduced diameter of 0.1 mm and directed onto the gel sample by mirror M1 at nearly normal incidence. The resulting fluorescence signal is efficiently collected by low f/number lens L1 situated with its focal plane intersecting the midpoint of the gel. The light leaving lens L1 is nearly collimated and passes through filters F1 and F2 which transmit the fluorescence at wavelengths longer than 600 nm but block light at the 543.5 nm excitation wavelength. Stop, S1, located just above mirror M1 is painted black and blocks specular reflections from gel and window surfaces from striking lens L1. A stray light shield further reduces diffusely scattered light from several sources otherwise incident upon filters F1 and F2. Lens L2 images the light onto a silicon photodiode detector positioned at its focal point. After electrophoresis and destaining, the gel is placed in a closed sample cell, preferably in the manner described hereinafter, which is then mechanically scanned at constant velocity in one direction, e.g., the Y direction, and repeatedly stepped between scans a small increment in the opposite direction, e.g., the X direction. The amplified voltage from the detector is converted into a signal with a 12 bit analog/digital (A/D) converter and stored and processed by an 80286 IBM AT clone computer.

The intensity of the fluorescence from each band in the gel is a function of the mass of DNA in the band. The resulting data can be processed by the computer to quantify the mass of the DNA in each of the scanned bands. DNA marker placements of known molecular weight and mass can be introduced in adjacent lanes to provide a means of calibrating fragment size versus migration distance and fluorescence intensity versus sample mass.

Commercially available lasers which produce constant output in the ultraviolet-visible spectrum at from about 250 nm to about 575 nm with a minimum power output of about 50 $\mu$W are useful in the invention. Such lasers include a helium neon laser, an argon ion laser, a helium cadmium laser, a CW argon-ion pumped tunable dye laser, and a CW diode pumped YAG laser.

A commercially available narrow band pass filter, such as filter F3, is selected to block incoherent background light produced in the gas discharge of the laser at wavelengths greater than the cut-on wavelength of filters F1 and F2, which is otherwise scattered by the gel into the fluorescence detection channel and sensed as a false signal. The specific narrow band pass filter F3 included in the embodiment depicted by FIG. 1 is a mercury line interference filter with a transmission wavelength of 546.1 nm, a peak transmission of 50%, and a 10 nm full width at half maximum (FWHM) bandpass (Oriel Corp., Model No. 56460). The filter is angle-tuned slightly to shift the peak transmission wavelength from 546.1 nm to 543.5 nm.

Focusing lenses, e.g. lens L3 shown in FIG. 1, are also commercially available and are selected to provide the desired laser beam spot size. The specific lens L3 included in the embodiment depicted by FIG. 1 is a 25 mm dia, 100 mm focal length anti-reflection (AR) coated, double convex glass lens Edmund Scientific Co., Catalog No. P32718).

There are two prerequisite conditions for achieving high performance level with instruments of the kind to which this invention relates. First, residual sources of unwanted light must be carefully controlled. Second, a low noise and drift measurement system must be provided.

Reduction of Unwanted Light

The first requirement is that room ambient light must be rigorously excluded. Next, specular (mirror-like) reflections of the incident laser light from gel and window surfaces must be carefully blocked by spatial filtering from striking filters such as F1 and F2. The filters otherwise fluoresce at longer wavelengths within the ethidium bromide stained DNA fluorescent wavelength interval of 600 nm to 750 nm. This is accomplished by the utilization of a nearly normal angle, e.g., an incidence of illumination with the sample which permits intercepting the reflecting beams with the blackened surface of stop S1 which is 10 mm×4 mm. In the FIG. 4 instrument, M1 is an aluminized front surface mirror 6.3 mm in diameter and 0.5 mm thick. A stray light shield such as that depicted in FIG. 4 further reduces diffusely scattered light from several sources incident upward upon filters F1 and F2. The stray beam light shield specifically utilized in the FIG. 1 device was fabricated from black cardboard, Bainbridge type 9026, with a 50. mm diameter aperture.

About 0.1% of the incident beam is also scattered by the gel into the field-of-view of the detection channel and, unlike the specular reflection, cannot be physically blocked. Filters F1 and F2 block the scattered incident beam which might otherwise produce a signal $10^4$ times as large as the sample fluorescence. Appropriate filters F1 and F2 can be selected from commercially available devices based on knowledge of the wavelength of the light in the scattered incident beam.

In the specific embodiment shown in FIG. 4, filter F1 closest to lens L1 was a 50 mm dia, dielectric interference long wavelength pass filter with a cut-on wavelength of 600 nm (Corion Corp., Catalog No. LL-600-R). Filter F2, positioned between F1 and Lens L2, was a 50 mm square glass absorption type long wavelength pass filter with a cut-on wavelength of 570 nm (Schutt type OG570). Filter F1 exhibits very low fluorescence at wavelengths greater than 600 nm and serves to attenuate the 543.5 nm scattered light by 90%, limiting the induced fluorescence in filter F2. Filter F2 provides almost complete absorption of the remaining 543.5 nm light transmitted by filter F1.

Lenses useful to perform the functions of lens L1 and lens L2 as shown in FIG. 1 are also commercially available. Lenses L1 and L2 are identical, biconvex, AR coated lenses 38.1 mm focal length, 50.8 mm dia, made of BR-7 low fluorescence glass (Newport Catalog No. KBX139). In a preferred embodiment, these are replaced with similar focal length and diameter plano-convex, asheric lenses in a commonly-employed condensor lens arrangement, i.e., with the curved sides facing filters F1 and F2, which produce less spherical aberration than obtainable with the biconvex lenses.

Another desideratum is to minimize fluorescence stimulated by the laser light in the sample cell windows and in the substrate supporting the gel which is passed by filters such as F1 and F2. After passing though the sample, the incident beam is absorbed by a low fluorescence substrate. An appropriate choice is a visible absorbing optical filter (Hoya Optics, Inc., Filter Type U-340). Interference fringes which otherwise modulate the gel fluorescence are suppressed for example, by maintaining a small angle of incidence, e.g., 5° or less, with respect to window and gel surfaces.

The average intensity level of the room ambient specular reflecting and other spurious light should not only be low compared to the fluorescent light levels from the gel, it also should not vary in a manner which mimics the signal response behavior arising from the separated DNA bands during scanning. A signal indistinguishable from sample fluorescence can be produced by very strong scattering of the laser beam excitation by large dust particles or imperfections in the gel substrate. Such scattering causes a detectable signal through the induced filter fluorescence mechanism, despite an otherwise sufficient filter transmission rejection ratio, for example, of $>10^6$.

The closed sample cell serves two purposes. It shields the gel from airborne dust particles, restricting them to the surface of the window which is sufficiently distant from the gel to be considerably out-of-focus. The residual fluorescence is then strongly attenuated by being poorly focused at the small area detector. The closed sample cell also reduces the loss rate of water from the gel by evaporation which otherwise causes moderate signal drift during the measurement period.

Low Noise and Drift Measurement System

Noise and drift in either the laser or the detection system directly impact the measurement. After warm-up, the helium-neon lasers preferably used in the invention are sufficiently stable and noise-free to eliminate any need to correct the fluorescent signal for source intensity fluctuation.

The commercial silicon photodiode detector referenced in FIG. 1 is selected to provide high quantum efficiency over the sample fluorescence emission spectrum, high stability, and low noise. An appropriate detector is a silicon photodiode with a photosensitive surface of 3.7 mm$^2$, a spectral response from 320 nm to 1100 nm, peak radiant sensitivity at 920 nm of 0.5 A/W, shunt resistance of $0.5 \times 10^9$ ohms, a noise equivalent power of $1. \times 10^{-14}$ (W/Hz$^{\frac{1}{2}}$) (Hamamatsu Type No. S1336-44BK). The output current from the small area, high quantum efficiency, silicon photodiode detector is amplified by a very high gain transimpedance amplifier, followed by a second amplifier stage providing further adjustable gain of $1 \times$ to $100 \times$. Alternatively, a photomultiplier may be utilized.

In summary, this invention reduces the potential measurement problems which would otherwise limit detectability to a level sufficiently low that very small variations in the stained gel background, e.g., of less than one percent, may become the factor limiting sensitivity or achievable detection limit.

The detection limit either visually observing ethidium bromide stained gels on a UV transilluminator or by photographing the fluorescent pattern is from about 0.3 ng/band to about 0.5 ng/band (500.pg/band) (17). In the absence of any gel background variation, the instrument shown in FIG. 1 would be capable of reliably detecting <1.0 pg/band. An important aspect of the invention, accordingly, includes improvements in gel uniformity.

Improved Gel Uniformity

One procedure for carrying out restriction fragment analysis of DNA or RNA is to cast a gel in the open, horizontal casting tray and perform the electrophoretic operation in a horizontal tank with the running buffer covering the top of the gel (17, 18).

High purity, low electroendosmosis agarose is mixed as a powder with water containing one of the several buffers designed to maintain a desired pH close to that of the running buffer. The mixture is heated to boiling which dissolves the agarose. The solution is typically allowed to cool to at least 65° C. before pouring to prevent warping the plastic casting trays that are commonly employed in widely available, commercial equipment. The gel is then poured into the open casting tray and allowed to cool to room temperature. A comb placed in the casting tray produces wells in the gel into which the sample is loaded. The thickness of the finished gel is determined by the volume of liquid cast and typically ranges from 2. mm to 10. mm. Alternately, the gel may be cast between glass plates which allow the gel thickness to be reduced to <2.0 mm, and the separation carried out in a vertical electrophoresis apparatus.

The ethidium bromide dye or other fluorophore may be added to the hot gel, to the running buffer, or the gel may be stained after the separating is completed. One of several simple destaining techniques (e.g., soaking the gel in water) is often employed. The contrast is enhanced since the background fluorescence of the free dye in the gel is reduced by a much larger factor (2× to 10×) than the loss in fluorescence of the dye bound to the DNA (<30%, typically).

Under ideal circumstances, a completely homogeneous gel of constant thickness would produce a perfectly uniform fluorescent background. Background correction would be carried out by simple subtraction assuming that the scanned fluorescent spectrum consists of fluorescence from the stained DNA bands linearly added to the uniform background fluorescence.

Actually, however, when gels prepared as outlined above are scanned at high resolution, for example, with a 0.1 mm diameter laser spot, there is considerable variation in the destained gel background. This variation consists of two principal components. Low spatial frequency variation (variation over a distance of several, e.g., two millimeters or more) is observed, over which is superimposed very sharp spike noise of much higher spatial frequency. The amplitude of the spike noise ranges from being barely detectable above the average gel background fluorescence level, to 2 to 3 orders of magnitude greater. The maximum noise spike amplitude can be many times the sample fluorescent peak amplitude. The spikes occur frequently along the scan. These effects restrict the detection to approximately 100-200 pg (0.1 ng-0.2 ng) per separated DNA band.

Visual inspection of slices through the gel suggest that much of the low frequency variation is due to the observable gel thickness variation. Gel thickness uniformity can be improved by 1. Using materials, e.g., glass, for the casting tray which allow pouring the gel at a temperature in excess of 65° C., preferably from about 70° C. to about 75° C.

2. Preheating the casting tray in an oven to a temperature which is equal to or up to about 5° C. above the pouring temperature.

3. Carefully leveling the casting tray before pouring the gel.

4. Pouring the gel at a temperature substantially the same as the casting tray preheat temperature.

A substantial reduction in both the amplitude of the noise spikes and the frequency with which they occur in the scanned spectrum can be achieved by filtering the hot gel in the liquid state before casting. Best results are obtained with a closed casting cell. An initial portion of the filtered gel is used to purge the closed cell of particulates in the enclosed air volume or which remain on the interior cell walls after cleaning and cell assembly.

Figure 25:
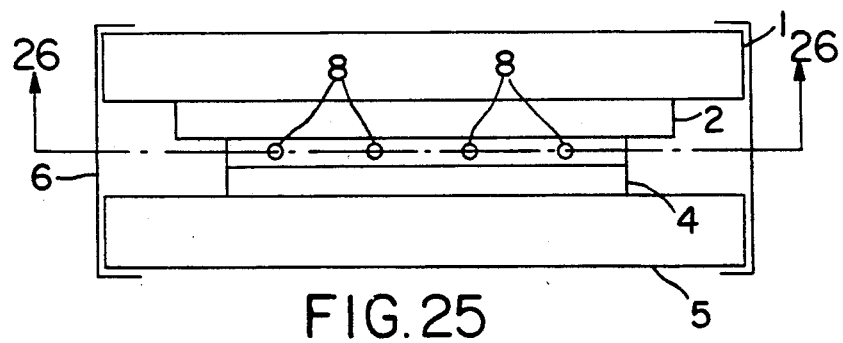
FIG. 25 is a top view of a cell gel casting assembly showing gel entry holes in the plate spaced gasket.

A preferred closed cell casting assembly, as illustrated by FIG. 25 includes an outer glass plate 1, a bottom gel casting plate 2, a spacer gasket 3, provided with gel entry holes 8, an upper gel casting plate 4, and an outer glass plate 5. The assembly is secured by tape 6.

Figure 26:
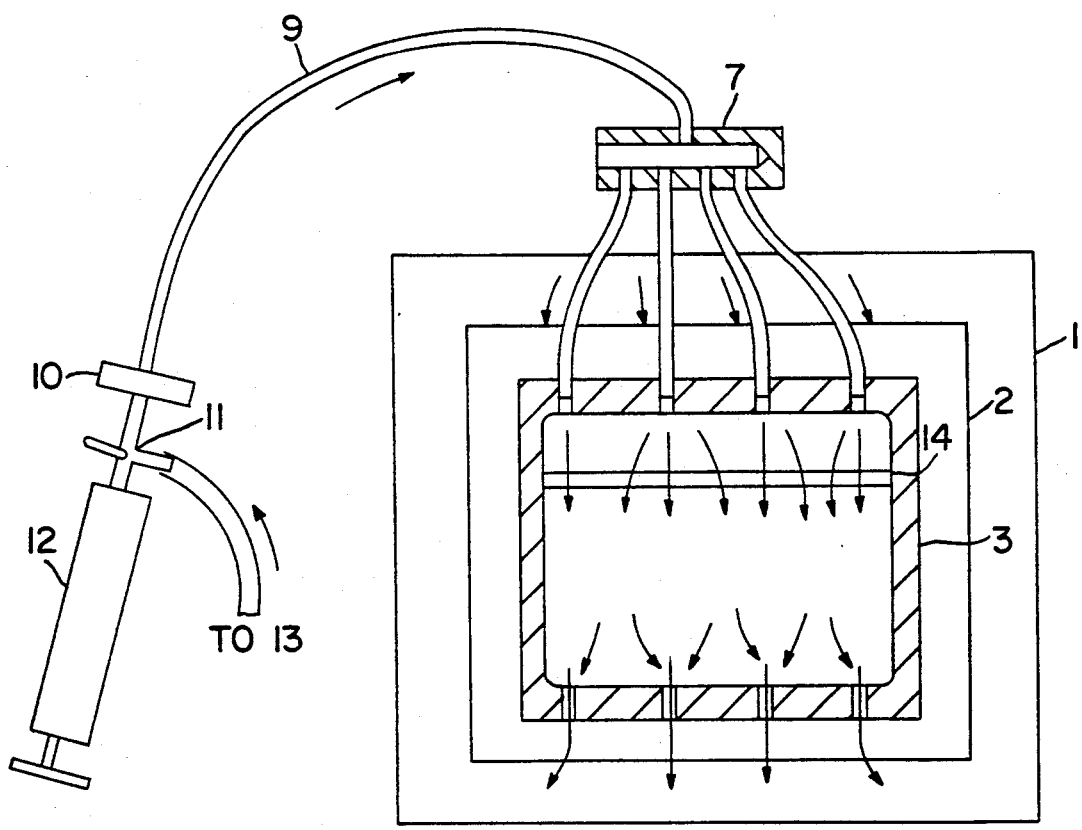
FIG. 26 is a view in section of the cell taken on the line 26—26 of FIG. 25 and of the syringe and gel filter method as utilized to introduce gel into the cell.

The filling of the cell is illustrated by FIG. 26. Hot liquid is drawn from a hot gel container 13 up into the syringe 12 through a 3-way tee valve 11. The tee valve is then reset to block flow back into the container and to allow flow through the filter. (Just prior to filling, a 20 cc to 30 cc volume of the hot gel is discharged through the filter into a waste container in order to remove particles in the 3-way tee valve and the delivery tube.) As the syringe plunger is depressed, hot, liquid filtered gel is distributed through delivery tube 9, manifold 7, and gel entry holes 8 at four points across the top of the gel casting cell, flows downward passing between the teeth of the casting comb, and out through the four holes in the bottom of the spacer gasket. Particulate contamination within the casting cell and on the inner surfaces of the gel cell casting plates is removed by the flow of the filtered gel. The liquid gel which passes out of the casting cell is contained in the outer volume formed by the two outer glass plates taped around the bottom and vertical edges. Filling continues until the gel level in the outer chamber rises to the top of the inner sample cell. The amount of gel purging is set by the volume of the outer chamber. The apparatus including the syringe and filter are preheated in an oven to 60°-65° C. The filling apparatus remains in the oven during the purging/filling operation which is performed through the open oven door.

The two glass plates 1 and 5 may be spaced apart a distance ranging from about 0.1 mm to about 10.0 mm by a teflon gasket. The resulting gel thickness is chosen to meet other requirements, e.g., robustness of low weight/volume gels, etc. The internal comb used to form the wells may be omitted and a separate stacking gel containing a comb to form wells can be cast at one end of the filtered gel, appropriate for either vertical or horizontal separations. Items 3, 7, 8, 9 and 14 are made of teflon. A 25 mm, 0.22 micron pore size disposable Nylon syringe filter (Corning type 25903) was used as item 10.

Another criterion for obtaining a uniform background and reduced spike noise is the need to destain the gel sufficiently. Gels placed in a distilled water bath preferably at a temperature of from about 18° C. to about 25° C. with mild agitation initially show poor uniformity during the first two hours of destaining. However, a rapid improvement in background uniformity after a minimum of two hours of destaining is observed. At a destaining time of four hours, the uniformity is somewhat further improved, the spike noise significantly reduced, and the average background fluorescence level reduced by at least eight-fold from the initial level observed at the start of destaining. This destaining procedure contrasts with the frequent practice of using static soaking for one hour or less which is insufficient to achieve maximum background uniformity or spike noise reduction. These simple steps lead to both considerable improvement in the uniformity of the gel background fluorescence and considerable reduction in the frequency and amplitude of the noise spikes.

It appears that the most probable cause of the spike noise is particulate contamination present in the reagents used to prepare the gel, or due to airborne particulates which have precontaminated the casting apparatus or settled into the liquid gel during cooling. Numerous shielding and filtering experiments have yielded results completely consistent with this explanation.

It is well established that air in a normal laboratory environment contains a high density of particulates with a continuous size distribution ranging from submicron to millimeter. As the particle size decreases, the number density increases. Only a tiny fraction of the total number of airborne particulates are large enough to be seen with the unaided eye. Since normal room air is in constant motion from induced convection, only the largest dust particles rapidly settle with the majority remaining in suspension.

The need to stringently control particulates is of paramount importance in some technologies such as semiconductor integrated circuit fabrication. This object is achieved by use of clean rooms which provide a working environment with greatly reduced particulate contamination. Casting the gels in the described manner or assembly of the gel cassettes (described next) in such clean rooms provides an alternative means for restricting particulate contamination.

The Gel Cassette

Another aspect of the invention provides a precast, prestained gel substantially free of particulate contamination in a cassette. Such cassettes permit electrophoretic separation in a vertical apparatus without removing the gel. After separation, the gel is directly scanned through the plates.

This aspect of the invention includes the discovery that stained gel can be scanned through properly chosen glass or plastic plates with retention of improved background uniformity. Additional fluorescence from the casting plates is minimized by using visible, preferably green light versus shorter wavelength excitation.

The use of gel cassettes is not new (19, 20). What is new in this invention is their specific application for the purpose of further improving the accuracy of the measurement of nucleic acid mass and further lowering the detection limit. These improvements in analytical performance are made possible by the use of a cassette in the following ways.

(1) Gel uniformity is improved by maintaining the plates in contact with the gel. The use of highly parallel, smooth and flat plates leads to a more uniform gel background by keeping the gel thickness more constant than can be obtained if the plates are removed given the elastic and easily deformable nature of agarose gels.

(2) A convenient means is provided of excluding ambient dust particles which otherwise settle onto the gel. These fluoresce within the instrumental detection bandpass even in the absence of staining.

(3) Evaporative loss from the gel is eliminated which uncontrolled causes drift in the fluorescence signal.

(4) It permits using thin gels (less than 1.0 mm thick) which would otherwise be too fragile to handle easily.

Accuracy is improved with thin gels in the following ways. The occurrence of particulate contamination which remains following gel filtering and casting cell purging is further reduced by simply lowering the gel volume. Fewer noise spikes improves the accuracy of post scanning data correction. A thinner gel also reduces the signal level of background fluorescence without lowering the level of sample fluorescence, improving the accuracy of background correction.

Reduced gel thickness over which fluorescence must be imaged onto the detector leads to several optical instrumental advantages which also contribute to improved accuracy. Among these are (a) improved rejection of undesirable fluorescence from dust particles on the surfaces of the plates, (b) a shorter optical path length through the gel leading to less absorption and scattering of the incident light beam exciting fluorescence, and (c) reduced beam diameter over the shorter optical path through the gel when using an incoherent light source focused upon the gel in a highly divergent, low f/no incident beam as an alternative to employing a highly collimated light source. Reduced beam width leads to improved spatial resolution and increased quantitative accuracy.

Thin gels provide other important performance advantages. Reduced temperature difference from the center of the gel to the edges in contact with the cassette walls arises from improved heat transfer over a shorter path length. Temperature-induced differences in fragment migration velocity in the separation direction are reduced which improves band sharpness and resolution. Reducing the gel thickness also reduces the cross-sectional area, increasing the electrical resistance through the gel between the electrodes normally employed. The increased resistance reduces the ohmic heating within the gel ($P = V^2/R$), further reducing the temperature differences within the gel, and further improving resolution. Alternatively, higher voltages (higher electric fields within the gel) may be employed which decrease the separation time and may improve band resolution, particularly for shorter nucleic acid fragments, by limiting band broadening produced by diffusion, a time-dependent effect which is reduced when the separation time is reduced.

One of several possible designs for the gel cassette is illustrated in FIGS. 27-29. The cassette consists of an upper plate 20, a lower plate 21, and spacers 22 which maintain the desired separation between the plates. Spring clips 23 attached along two edges hold the cassette together pressing the upper and lower plates against the spacers with sufficient force to prevent leakage during the process of filling the cassette with hot liquid gel. Alternatively, the upper and lower plates may be permanently bonded to the spacer.

The entire cassette can also be injection molded in plastic, as indicated by FIGS. 31-33. The ends of the cassette are sealed with caps 24 which are easily removable, exposing the ends of the gel as the first step when a separation is to be performed. Suitable materials for both plates must have high optical transmission, adequately low and uniform fluorescence at the excitation wavelengths employed, and be capable of a surface finish which is flat, smooth, and sufficiently free of surface defects which can otherwise cause light scattering severe enough to affect optical performance. Suitable plates can be fabricated from such glasses as quartz, Pyrex and BK-7 and such plastics as UV transmitting acrylic plastic (Plexiglas), and polystyrene, among other possible choices.

The procedure for filling the cassette with gel is similar to that previously described. Standard optical surface cleaning procedures are adequate to clean the plates before assembly with the addition that final rinsing be performed with double distilled water that has been filtered to remove particles greater than 0.2 um. The wet plates should be dried in an environment as dust-free as possible. Particulate contamination is minimized during drying and subsequent cassette assembly if performed in a filtered air environment such as provided by a clean room facility or by use of a clean bench or hood which provides a continuous flow of clean air over the work area which has been filtered to eliminate particulate contamination.

Figure 35:
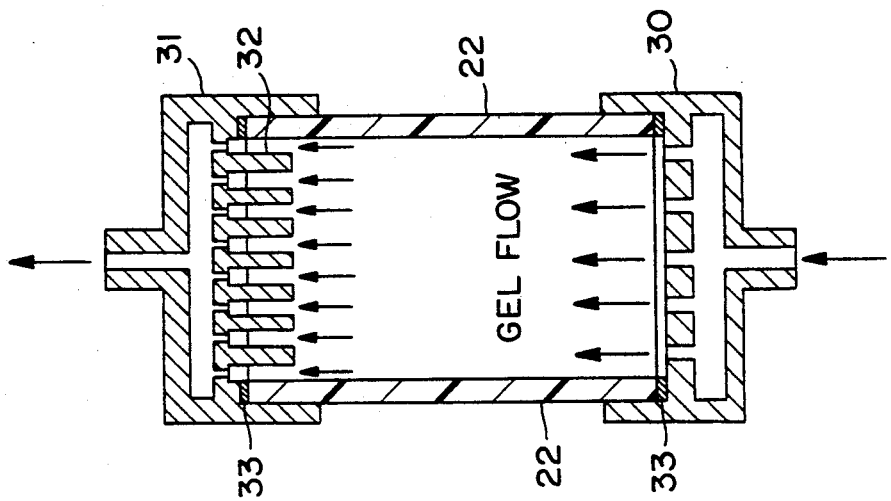
FIG. 35 is a sectional view of the cassette taken on line 35—35 of FIG. 34.
Figure 34:
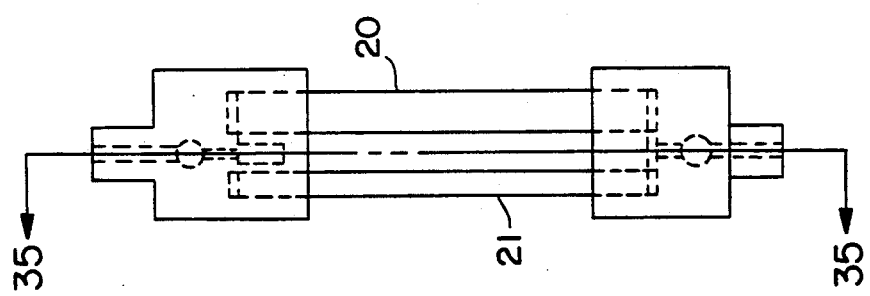
FIG. 34 is a view illustrating the cassette of FIG. 27 vertically positioned for filling.

The procedure described earlier is modified to minimize gel wastage and to avoid the need to remove hardened gel from the outer surfaces of the upper and lower cassette plates following filling. These modifications are important in large quantity production. The cassette is prepared for filling as shown in FIGS. 34–35. The lower manifold 30 introduces the hot liquid gel and distributes it evenly across the width of the cell. The upper manifold 31 facilitates removal of the purging gel evenly across the width of the cassette. The upper manifold 31 contains a comb 32 which casts sample loading wells into the gel at the upper end of the cassette. Alternatively, the walls may be formed using a stacking gel cast in a separate, later step. Elastomer gaskets 33 in the manifolds contact the ends of the cassette and provide a seal sufficient to avoid gross loss of the hot filtered gel. The manifolds are clamped to the ends of the cassette to support it in the vertical position during filling and to produce the seal.

The filling operation is carried out in a temperature environment which is above the gel solidification temperature, e.g., 50° C. to 70° C. for normal agarose gels. All components in contact with the gel are allowed to reach this temperature range before filling begins. Means for handling and filtering large volumes of liquid gel appropriate for large scale production may be substituted for the syringe and 0.2 $\mu$m filter shown in FIG. 26 to achieve the same ends. Several cassette volumes of gel are still employed as a purging means for removing residual particulate contamination from the cassette, followed by final filling. Prior to filling, dye is added to the hot liquid gel at a temperature such that the dye is not adversely affected, e.g., below 80° C. for ethidium bromide in an agarose gel, followed by brief stirring to insure uniform mixing.

After filling, the cassettes are allowed to cool until the gel solidifies and the manifolds and casting comb are removed. Small amounts of excess gel on the surfaces of the cassette, if any, are also removed and the end caps applied to cover the ends of the cassette.

An electrophoretic separation is performed in the normal manner in a vertical separation apparatus. The cassette end caps are removed and the cassette positioned vertically with the exposed gel at the lower end in contact with the lower running buffer solution. Samples are pipetted into the wells in the upper end before filling the separation apparatus with buffer solution in the upper reservoir. After separation is complete, the end caps are applied in order to limit gel shrinkage by evaporation.

Figure 36:
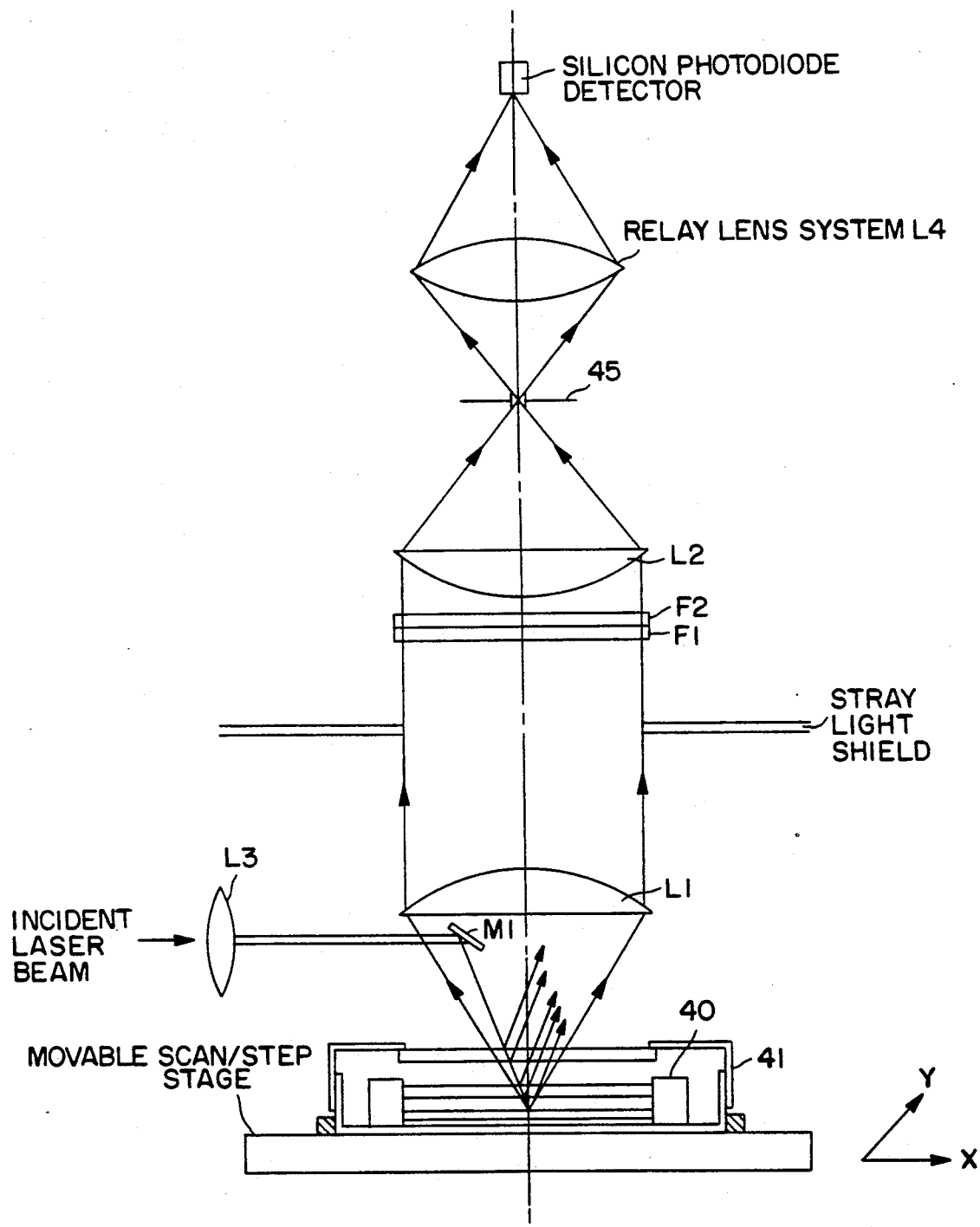
FIGS. 36 and 37 show a cassette of the kind illustrated by FIGS. 27 and 31 in position in a cassette holder for scanning, together with the associated scanning and fluorescence detecting elements.
Figure 37:
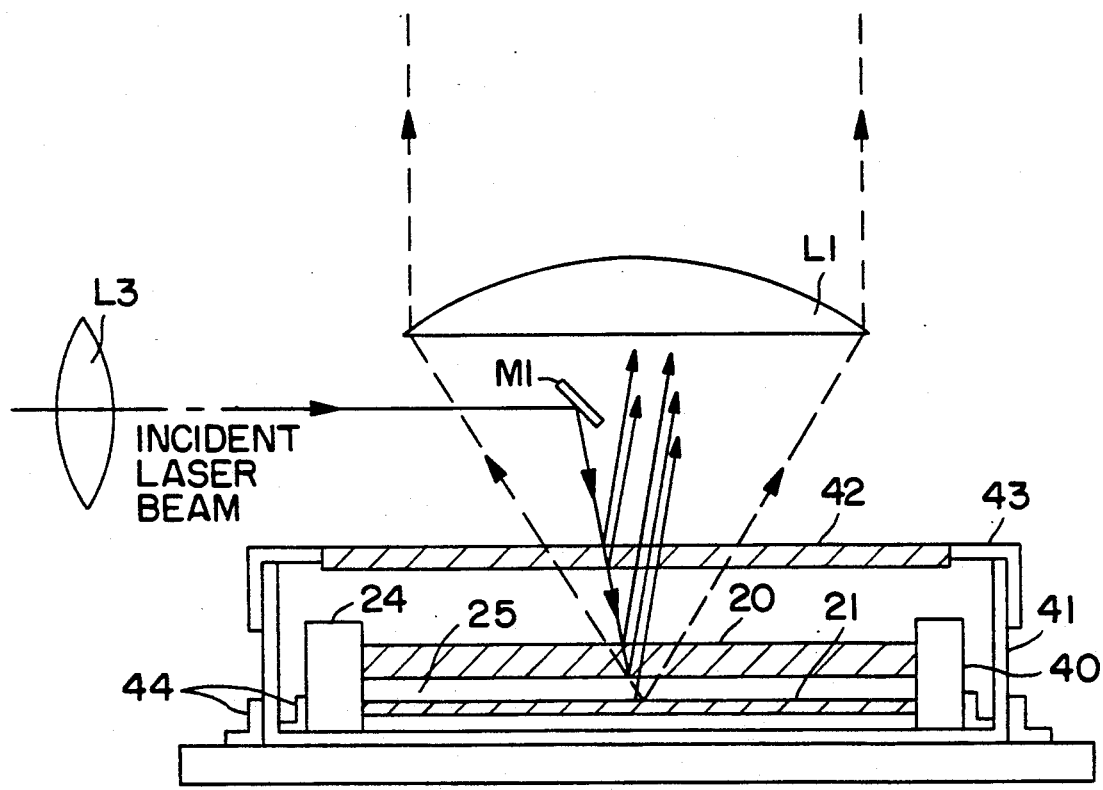

Fluorescence scanning is begun by placing the cassette 40 into the cassette holder 41 shown in FIGS. 36 and 37. The lid of the holder 43 has a window 42 which prevents large dust particles from settling onto the cassette during the measurement. The holder 41 also provides a means of locating the cassette and cassette holder in a known position using positioning rails 44 with sufficient accuracy to permit scanning without further operator intervention. Just before placing the cassette into the holder the outer surfaces of the upper and lower plates are rinsed with filtered water and wiped clean with lint-free cloth or allowed to air dry in a covered container which limits exposure to large airborne dust particles. The purpose of this final cleaning step is simply to remove very large dust particles which might produce noise spikes with a width that exceeds the limit for detection and removal in the post measurement signal processing. Alternatively, a protective foil or wrap could be provided covering the two plates which would be removed before placing the cassette in the holder.

Reducing the thickness of the gel six-fold or more to equal or less than 0.5 mm requires modification of the optical system shown in FIG. 4. Laser illumination with highly parallel, monochromatic light can lead to the well-known behavior of interference fringing in its passage through two or more highly parallel interfaces of differing index of refraction, e.g., air-to-cassette plate, plate-to-gel. This effect can modulate the intensity of the incident beam producing, in turn, an undesirable fluctuation in the sample fluorescence signal. At sufficient angle of incidence, the interference effect can be avoided. For a 0.1 mm diameter laser beam, the required angle of incidence for a 3.00 mm thick gel is less than 3 degrees but increases to 10 degrees for a gel 0.4 mm thick. FIG. 26 shows the modified optical detection system with mirror M1 rotated to provide the increased angle of incidence of 10 degrees. Light reflected from the several surfaces as shown in FIGS. 36 and 37 is no longer blocked by the stop, S1, but is now intercepted at other points in the optical system.

Use of the cassette introduces another optical element, the upper plate. Dust particles on its surface are observed to fluoresce within the spectral bandpass of the detection system, producing high spatial frequency noises spikes identical to those produced by particulate contamination within the gel. The the reduced gel thickness provides an opportunity to strongly attenuate the fluorescence from these particles on the surface of the upper plate without affecting the sample fluorescence. Greatly reducing the amplitude of the noise spikes increases the accuracy of their removal from the data. The reduced gel thickness reduces the depth-of-field over which the optical system must efficiently image the fluorescence signal. The small diameter pinhole 45 acts primarily as an aperture stop, limiting the amount of light originating from the out-of-focus top surface of the upper plate which can pass through it. Light passing through pinhole 45 can be imaged onto the detector with relay lens system L4 consisting of one or more optical elements. Alternatively, the detector may be positioned immediately behind the pinhole. Given proper lens design to limit spherical aberration, almost all the light collected by lens L1 over a depth-of-field of 0.4 mm can be imaged by lens L2 through an aperture of 0.5 mm. If the upper plate is 4.0 mm thick, fluorescence from dust on the surface originates 4.20 mm behind the focal plane of L1 positioned at the center of the gel. Less than 2% of the unfocused light from the top surface is then able to pass through the pinhole. Such a large attenuation can only be achieved for a 3.0 mm thick gel by using an unacceptably thick cassette upper plate since the pinhole diameter must be much greater to pass light over the larger depth-of-field.

The lower plate can be thinner than the upper plate in order to maximize transfer through it of heat generated in the gel during the separation. The incident laser beam passing through the gel next passes through the lower plate. It is absorbed by a layer of flat black paint applied to its outer surface. Alternately, the beam may be allowed to pass out of the gel cassette where it is absorbed on the light absorbing bottom surface of the cassette holder.

Improved Data Reduction

An important step in processing the acquired data is accurate correction for the remaining noise spikes. Sharply restricting particulate contamination of the gel, both in the process of casting it and in subsequent handling and scanning procedures, is an essential requirement for attaining highly accurate background correction of the scan data and substantial reduction of the detection limit. Filtering the hot gel reduces the number of particles and limits the remaining particle size, both of which are important. The remaining noise spikes are now much smaller in amplitude, and occur less frequently, both of which improve the accuracy of the spike removal process.

Under these improved conditions, the remaining noise spikes can be reliably identified since their full width at half maximum (FWHM) is less than the width of a separated DNA band. The width of a separated DNA band depends upon a number of factors which include the molecular weight of the DNA fragment, the percent weight by volume of agarose in the gel, the voltage and running time utilized in the electrophoretic separation, the sample size with respect to both weight and volume, and, to some extent, the dimensions of the sample well. Observed sample fluorescent peaks are rarely less than 0.3 mm FWHM under the separation conditions summarized in Table 1. The noise spikes which arise from the remaining smaller size stained particles are uniformly characterized by a FWHM limited by the diameter of the laser spot which is much larger than the particle size. Noise peaks are observed to have a FWHM of 0.1 mm to 0.2 mm for a 0.1 mm diameter spot.

Under other separation conditions, sample fluorescent bands less than 0.3 mm FWHM can occur. The laser beam width can accordingly be further reduced, again allowing the narrower noise spikes to be detected. The 2:1 ratio in peak widths permits identifying the noise spikes by first locating every peak and then measuring its width at the half height point. Each noise spike is then removed by truncation at its base. This process is performed by using a consistent set of rules for deciding how to identify a noise peak and how to select the points at the base of the noise spike for truncation. The process is automated and executed by computer.

Computer Rules for Identification and Removal of Noise Spike

A. Introduction

Each instrumental scan over the gel sample covers a total physical distance, Ymax, in the electrophoretic migration or lane direction in a total of Jmax measurements made at equal time intervals over the scan. The fluorescence intensity, F(J), is the average of K separate, rapid, sequential A/D conversions and lies between 0 and an upper limit of 4095 counts imposed by the 12 bit A/D convertor. Representative values for measurements with the instrument shown by FIG. 4 are Ymax=10.0 mm, Jmax=650 data points, K=60 sequential A/D conversions averaged to yield one data point. Constant scan velocity is assumed with the scan distance, Y taken as Y=(J/Jmax) X Ymax.

Noise spikes are identified as those peaks which have a full width at half maximum (FWHM) which exceeds a selected limit, FWHMmax. Peaks which are saturated at the 12 bit A/D converter limit of 4095 counts are considered to be noise peaks, the assumption being that the signal gain was set properly at the beginning of data acquisition to avoid saturation on a sample fluorescent peak.

B. Procedure for Unsaturated Noise Peaks (Spikes)

The procedure for identifying and removing saturated noise spikes is illustrated by FIGS. 38–42 and consists of the following steps.

(1) Smoothing the data—Each point in the data set is replaced with the five point average of itself and the four immediately adjacent points:

$$F(J) = [F(J-2) + F(J-1) + F(J) + F(J+1) + F(J+2)]/5 \quad (1)$$

(2) Peak identification—A peak at Jp is identified as a point satisfying the following criteria:

$$\begin{aligned} &F(Jp-4) < F(Jp-3) \text{ and} \\ &F(Jp-3) < F(Jp-2) \text{ and} \\ &F(Jp-2) < F(Jp-1) \text{ and} \\ &F(Jp-1) < \text{ or } = F(Jp) \text{ and} \\ &F(Jp) > \text{ or } = F(Jp+1) \text{ and} \\ &F(Jp+1) > F(Jp+2) \text{ and} \\ &F(Jp+2) > F(Jp+3) \text{ and} \\ &F(Jp+3) > F(Jp+4) \end{aligned} \quad (2)$$

Figure 38:
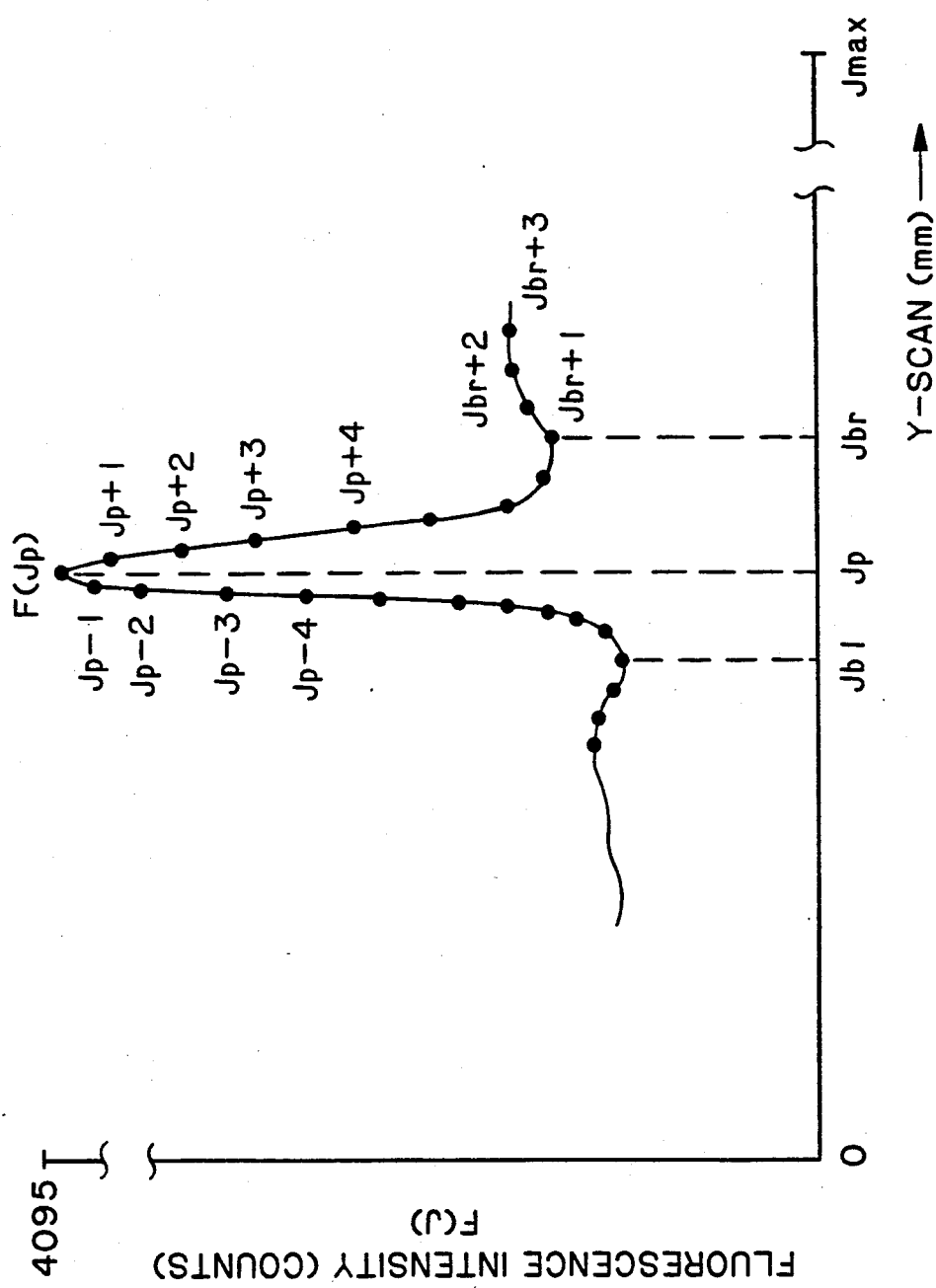
FIGS. 38–42 illustrate procedures for peak removal.
Figure 39:
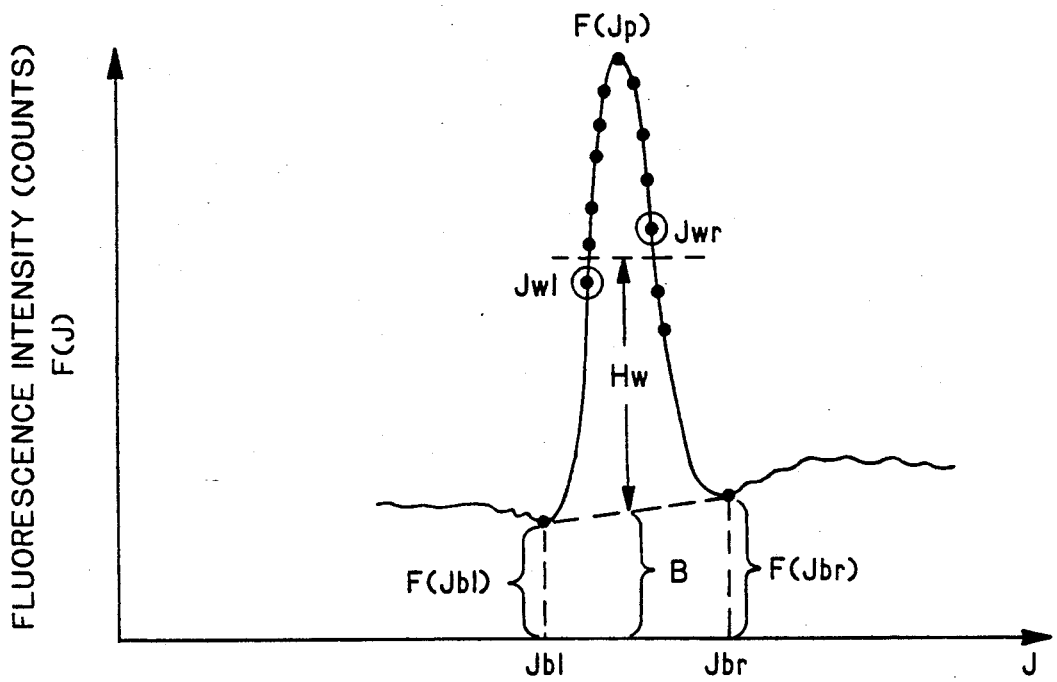
Figure 40:
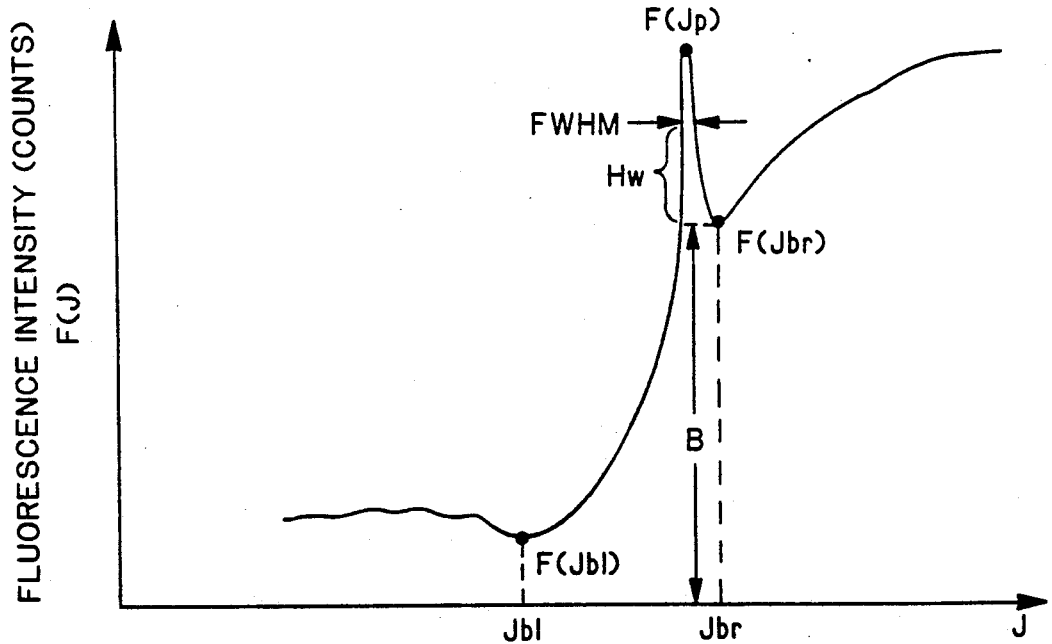

(3) Base point identification—Base points on either side of a peak are chosen as the points where the baseline begins to increase moving away from the peak (see FIG. 38). The criterion for the right base point, Jbr, is:

$$\begin{aligned} &F(Jbr) <= F(Jbr+1) \text{ and} \\ &F(Jbr+1) <= F(Jbr+2) \text{ and} \\ &F(Jbr+2) <= F(Jbr+3) \end{aligned} \quad (3)$$

with a corresponding criterion for the left base point, Jbl.

(4) Choosing the base of the peak—In order to measure the width of the peak at half height, a point representing the base of the peak must be chosen which is subtracted from the fluorescence signal at the peak, F(Jp). For a peak on a relatively flat background (see FIG. 39), the base, B, is taken simply as:

$$B = [F(Jbr) + F(Jbl)]/2 \quad (4)$$

However, when the peak sits on a steep, rapidly changing background (FIG. 40), this value fails to lead to an appropriate measure of the half width, and the larger of the two signals F(Jbl) or F(Jbr) is selected as B instead. If the ratio of the net peak height to the difference in base height is sufficiently great, Eq. (4) is used. More exactly, this rule is expressed as:

$$Rr = \text{abs. value of} \\ \{[F(Jp) - F(Jbr)]/[F(Jbr) - F(Jbl)]\}, \quad (5)$$

$$Rl = \text{abs. value of} \\ \{[F(Jp) - F(Jbl)]/[F(Jbr) - F(Jbl)]\}, \quad (6)$$

then if $$Rr >= Rl \text{ and } Rl >= Rl, \quad (7)$$

(where Rl is typically 2.0), use Eq. (4) to calculate B. If Eq. (7) is not true, then pick B as the greater of F(Jbl) or F(Jbr).

(5) Determining the peak width at half height—The FWHM is found by selecting those values of J for which F(J) is closest to the half height, Hw, taken as:

$$Hw = B + \tfrac{1}{2}[F(Jp) - B] = \tfrac{1}{2}[F(Jp) + B] \quad (8)$$

In order to avoid the extra steps associated with interpolating between data points immediately above and below Hw, the half height value of J at the right side of the peak, Jwr, corresponds to the first value of F(J) which is just equal or greater than Hw moving to the right from the peak, and on the left, Jwl is taken as corresponding to the first value of F(J) which is just equal or less than Hw moving in the opposite direction from the peak. Then:

$$FWHM = Jwr - Jwl \tag{9}$$

(6) Identification of a noise peak—The final step is to test whether:

$$FWHM <= FWHMmax, \tag{10}$$

where FWHMmax is the maximum allowable peak width for a noise peak expressed as an interger number of data points. FWHMmax will vary as Jmax and Yscan change. It is first calculated as:

$$FWHMmax = (Jmax/Ymax) \times Wmax, \tag{11}$$

where Wmax is the maximum permissible width of a noise peak expressed in mm.

Figure 41:
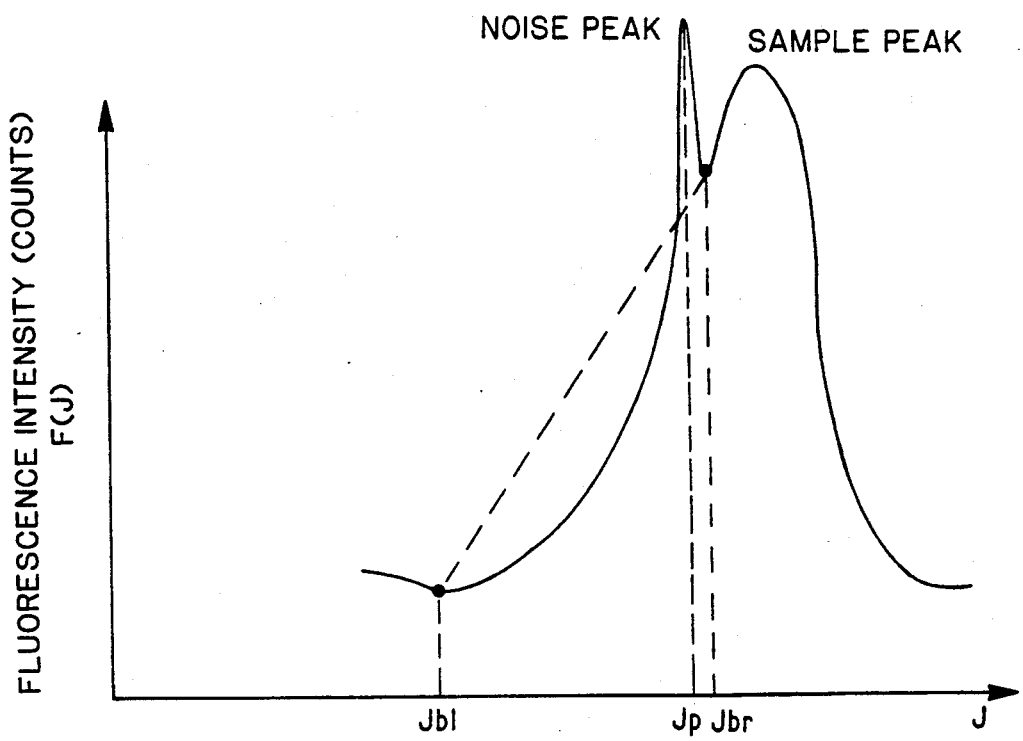
Figure 42:
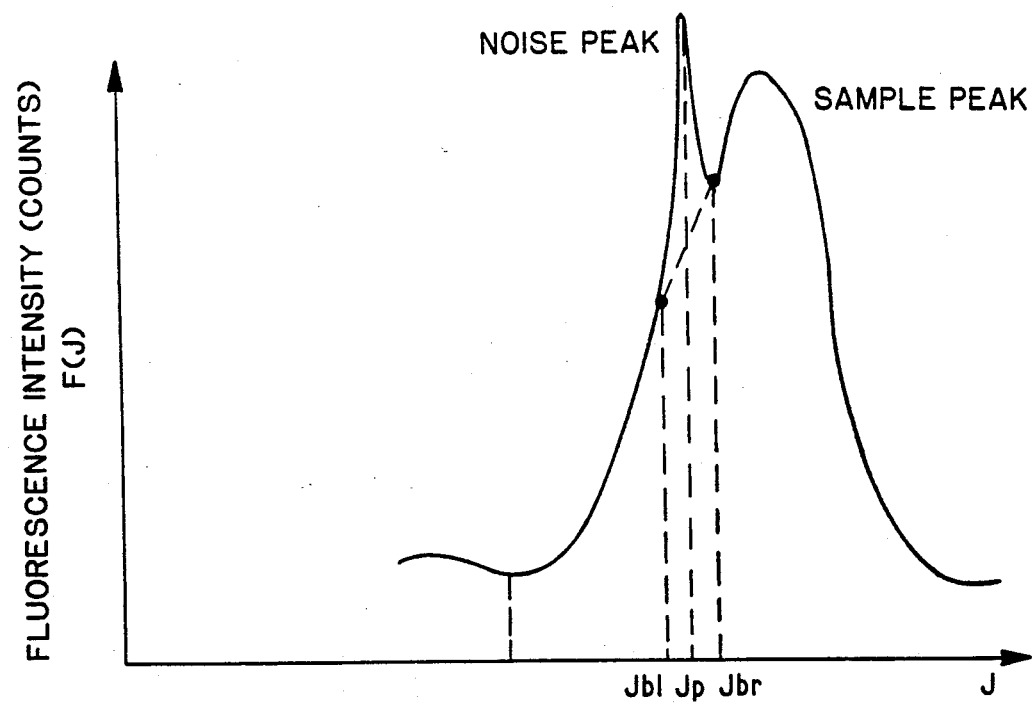

(7) Revised base points for use in noise peak truncation—The base points identified earlier on either side of the noise peak are normally used as the starting and ending points for peak truncation by linear interpolation. However, when Jbl and Jbr are located at very unequal distances from the peak, this procedure can lead to over or under compensation as illustrated in FIG. 41. Better correction is obtained in this instance by substituting a new base point for the one further from the peak at a distance equal to the closer base point. See FIG. 42. The test is:

$$\text{If } (Jbr-Jp) > (Jp-Jbl) \text{ and if}$$
$$(Jbr-Jp)/(Jp-Jbl) > R2 \tag{12}$$

(R2=1.5 typically), then the revised right-hand base point, Jbr, is:

$$Jbr = (Jp-Jbl) + Jp = 2Jp - Jbl. \tag{13}$$

A similar procedure is used to find the revised left-hand base point if $(Jp-Jbl)/(Jbr-Jp) > R2$.

(8) Noise Spike Removal—Data points representing the noise spike between the basepoints are replaced by the straight line drawn from F(Jbl) to F(Jbr):

$$\text{For } J = Jbl \text{ to } Jbr, \; F(J) = M \times J + C, \text{ where} \tag{14}$$

$$M = [F(Jbr) - F(Jbl)]/(Jbr - Jbl), \text{ and}$$
$$C = F(Jbr) - M \times Jbr. \tag{15}$$

C. Modified Procedure for Saturated Noise Peaks

The procedure is identical to that above for unsaturated noise peaks except for the following modifications:

(1) Locating the center of the saturated peak—If F(J)=4095 is encountered while testing for peaks in (2) above, a noise peak position, Jp, is assigned to that value of J which lies half way between the first and last values of J at which saturation begins and ends.

(2) Base point identification—Base points are found in the same manner as in (3), but the test is begun at the first unsaturated point on either side of Jp.

(3) Remaining modifications—After identifying the basepoints, steps (5), (6) and (7) above are skipped, and noise truncation step (8) is immediately carried out.

Several factors may seriously degrade the accuracy of this procedure for noise spike identification and removal. The detector response time must be short enough for a given scan speed to allow detection of the sharp peak without undue broadening. The dimension of the scanning illumination spot must be maintained considerably smaller than the width of a separated DNA band in the lane or separation direction. The frequency with which the remaining dust particles occur must be low enough so that the probability of illuminating two or more simultaneously is small. Reducing the amplitude of the noise spikes by reducing particulate size substantially improves the accuracy of the baseline truncation procedure.

EXAMPLE I

A 50 mm×70 mm×3.0 mm thick agarose gel was cast employing all of the procedures described herein for improving gel background uniformity. Table 1 summarizes the details of the gel sample preparation, electrophoresis separation, and the subsequent destaining.

TABLE 1

| | |
|---|---|
| Sample: | Hind III/Lambda DNA. 41., 4.1, 0.41, 0.1, 0.041 ng sample masses, 4.0 μl loading volume. |
| Gel: | 1.0% agarose, prestained with 0.5 μg/ml ethidium bromide added to the gel at 80° C. Gel thickness approx. 3 mm. IBI UV casting comb with wells 2.5 mm wide × 1.0 mm thick, with teeth spaced 5.0 mm apart. |
| Electrophoresis Apparatus: | IBI Model MPH Multi-Purpose Horizontal. |
| Running Buffer: | 1.0 × TBE |
| Loading Buffer: | 0.1% bromophenol blue, 0.1% xylene cyanol, 100 mM EDTA, 1% SDS, 50% glycerol in water. |
| Separation: | 100 v for 35 minutes, 50–100 ma current. |
| Destaining: | 4 hours in 600 ml distilled water with magnetic stir bar agitation. |
| Sample Preparation: | IBI HindIII/Lambda DNA marker, 510. μg/ml. |
| step (1) - 2 μl of marker | = 1,020 ng + $\frac{18 \mu l \text{ water}}{20 \mu l \text{ of 51 ug/ul}}$ |
| step (2) - 2 μl of 51 ug/ul | = 102 ng + $\frac{18 \mu l \text{ of water}}{20 \mu l \text{ of 5.1 ng/}\mu l}$ |
| step (3) - 2 μl of 5.1 ng/ul | = 10.2 ng + $\frac{18 \mu l \text{ of water}}{20 \mu l \text{ of 0.51 ng/}\mu l}$ |
| step (4) - 2 μl of 0.51 ng/μl | = 1.02 ng + $\frac{18 \mu l \text{ of water}}{20 \mu l \text{ of 0.051 ng/}\mu l}$ |
| step 5 - | 4 μl of 5.1 ng/μl = 20.4 ng + 4 μl of loading buffer + $\frac{12 \mu l \text{ water}}{20 \mu l \text{ of 1.02 ng/}\mu l}$ × 4 μl = 4.1 ng sample size |

TABLE 1-continued step (6) - 4 µl of 0.51 ng/µl = 2.04 ng +

4 µl of loading buffer +

$$\frac{12 \text{ µl water}}{20 \text{ µl of 0.102 ng/µl}} \times 4 \text{ µl} = 0.41 \text{ ng sample size}$$

step (7) - 4 µl of 0.051 ng/µl = .204 ng +

4 µl of loading buffer +

$$\frac{12 \text{ µl water}}{20 \text{ µl of 0.0102 ng/µl}} \times 4 \text{ µl} = 0.041 \text{ ng sample size}$$

The HindIII restriction fragment band pattern is shown in Table 2.

TABLE 2

| Fragment (band) No. | Base Pairs | MW (kdal) | Percentage of Sample Mass | Mass/Band for 4.1 ng sample (ng) |
|---|---|---|---|---|
| 1 | 23,130 | 15,428 | 47.7 | 2.0 |
| 2 | 9,419 | 6,283 | 19.4 | 0.79 |
| 3 | 6,557 | 4,374 | 13.5 | 0.55 |
| 4 | 4,371 | 2,916 | 9.00 | 0.37 |
| 5 | 2,322 | 1,549 | 4.79 | 0.20 |
| 6 | 2,028 | 1,353 | 4.18 | 0.17 |
| 7 | 564 | 376 | 1.16 | 0.048 |
| 8 | 125 | 84 | 0.26 | 0.011 |
| Total: | 48,516 | | 100% | 4.1 ng |

The assumed mass of DNA in each separated band is taken as the mass of the sample times the fractional molecular weight of that band, e.g., for band #1, 4.1 ng×(23,130/48,516)=2.0 ng.

EXAMPLE II

Figure 5:
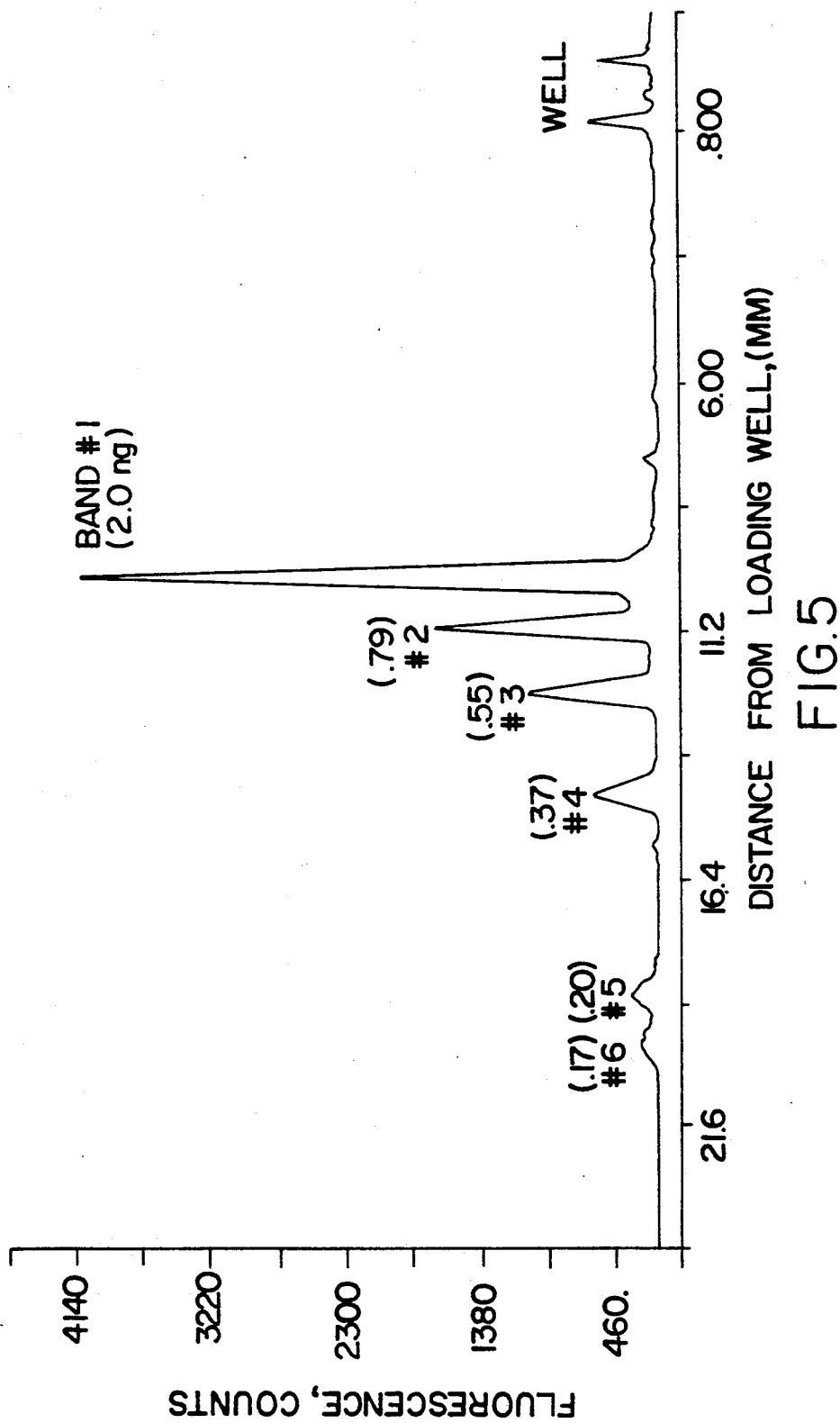
FIG. 5 shows a composite of three separate scans of a 4.1 ng separated sample.
Figure 6:
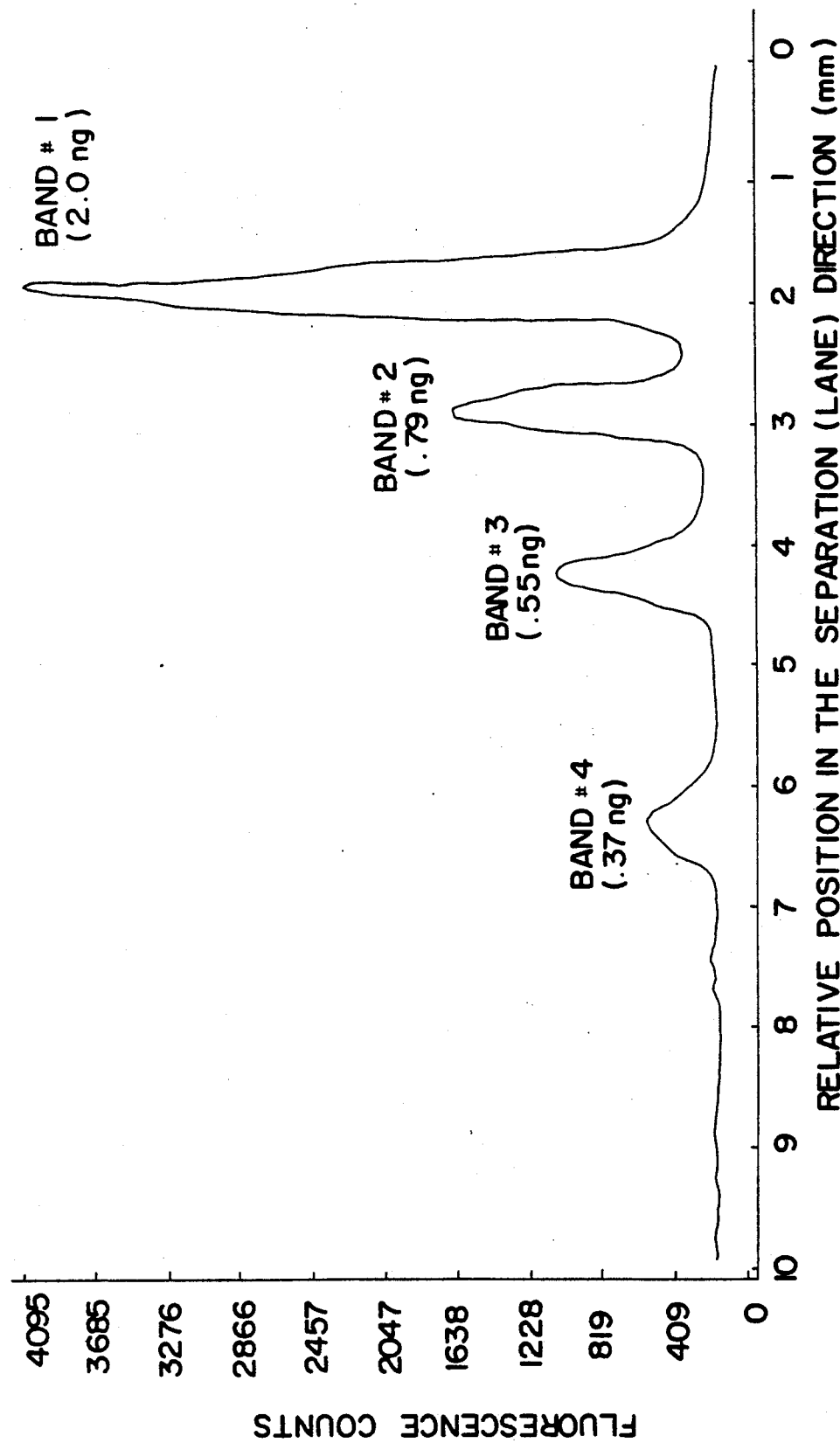
FIG. 6 represents one of the individual scans which was used to form the composite showing in FIG. 5.

FIG. 5 shows a composite of three separate scans, utilizing the instrument as shown in FIG. 4, of the 4.1 ng separated sample described in Example I. (The scanning apparatus has a 10.0 mm maximum scan range in the lane direction requiring repositioning of the gel between scans.) FIG. 6 represents one of the individual scans which were used to form the composite and shows excellent signal-to-noise. (The first three bands can also be seen using a mid-UV transilluminator.) Scans of the 41 ng sample lane produced essentially the same results with virtually no evidence of spike noise.

Figure 7:
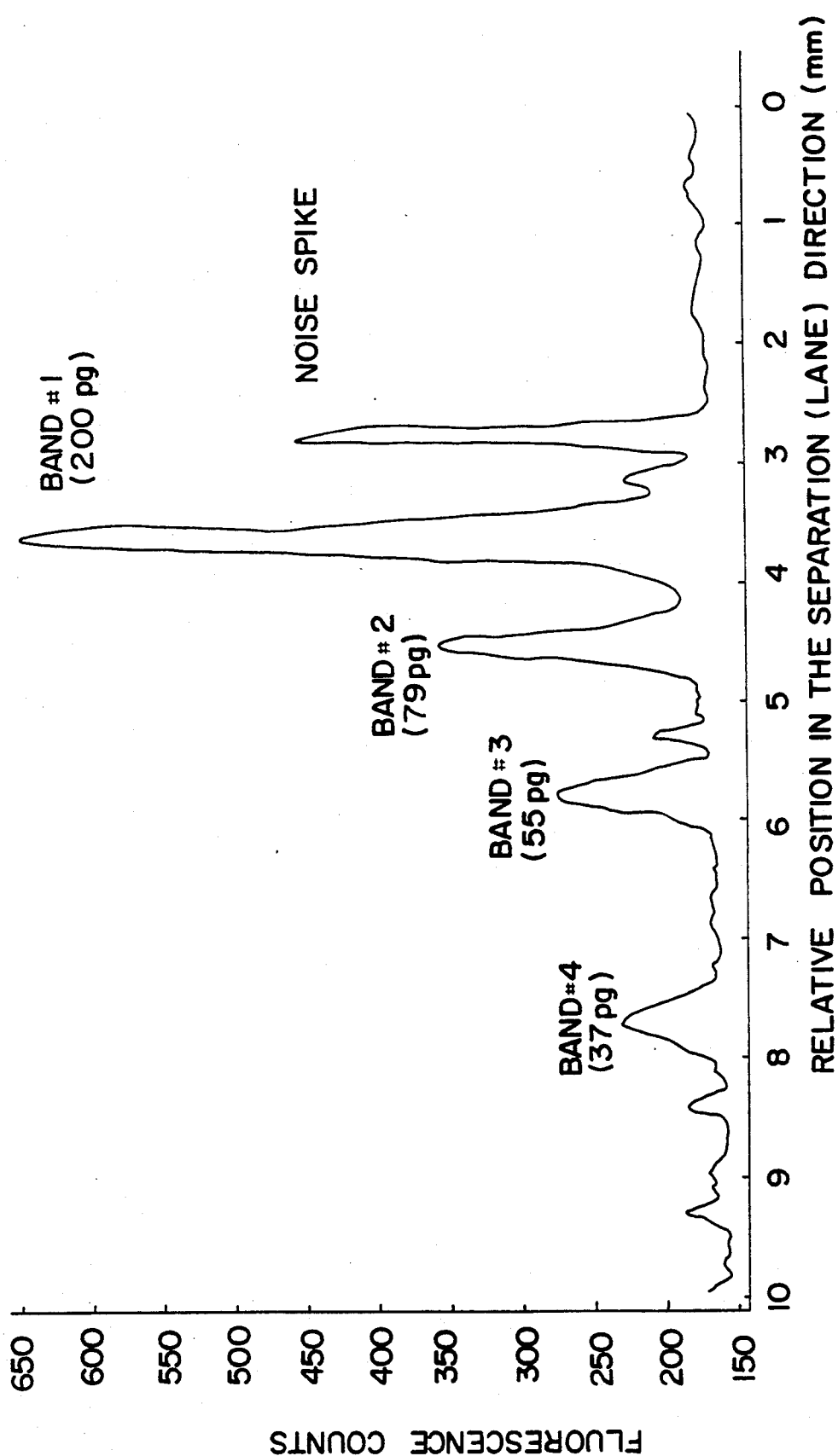
FIG. 7 shows bands 1–4 as shown in FIG. 5 when the sample concentration is reduced 10-fold to 0.41 ng.

FIG. 7 shows bands #1–#4 when the sample concentration is reduced by 10× to 0.41 ng. At this concentration the bands are no longer visually detectable. Band #4 with an estimated mass of 37 pg is clearly present. The 10× increase in gain, compared to that used for scanning the 4.1 ng sample, leads to greater baseline noise. A large amplitude noise spike is evident. Note that the spike is narrow compared to the sample bands.

EXAMPLE III

Figure 8:
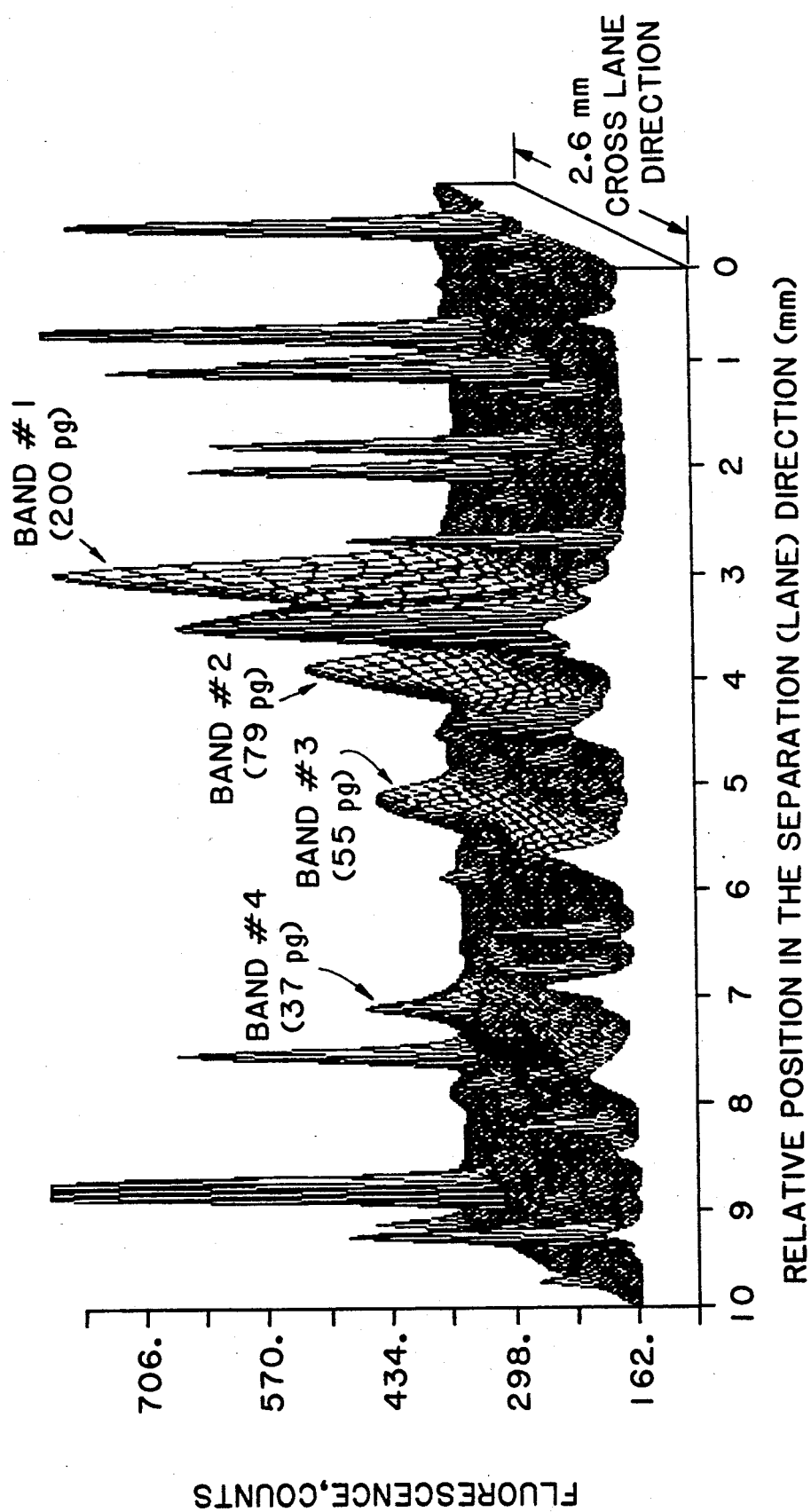
FIG. 8 is a three-dimensional plot of 14 repeated scans spaced 0.2 mm apart in the X-direction normal to the separation or lane direction.
Figure 9:
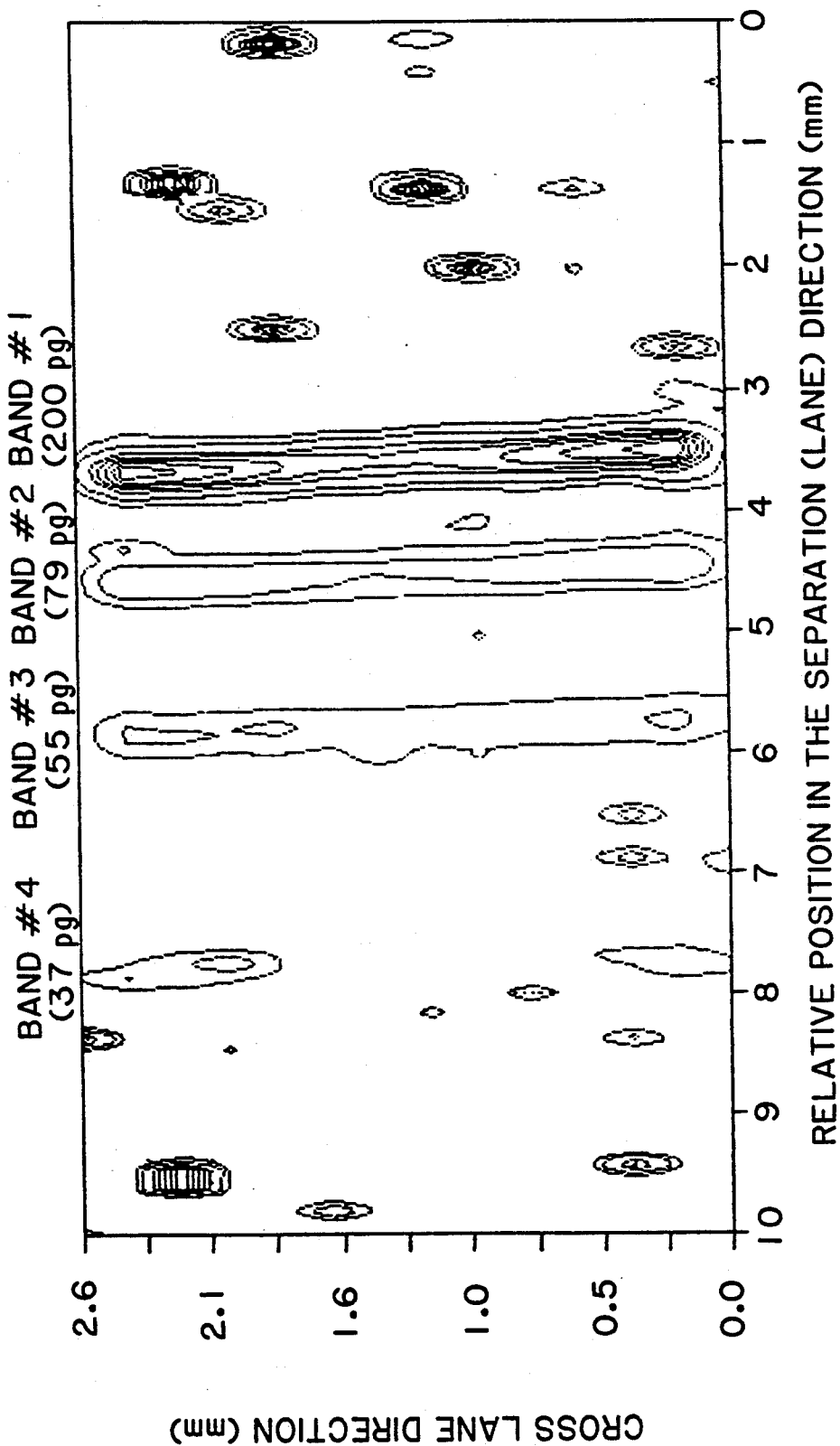
FIG. 9 shows a contour plot depicting the same data as that reported in FIG. 8.
Figure 10:
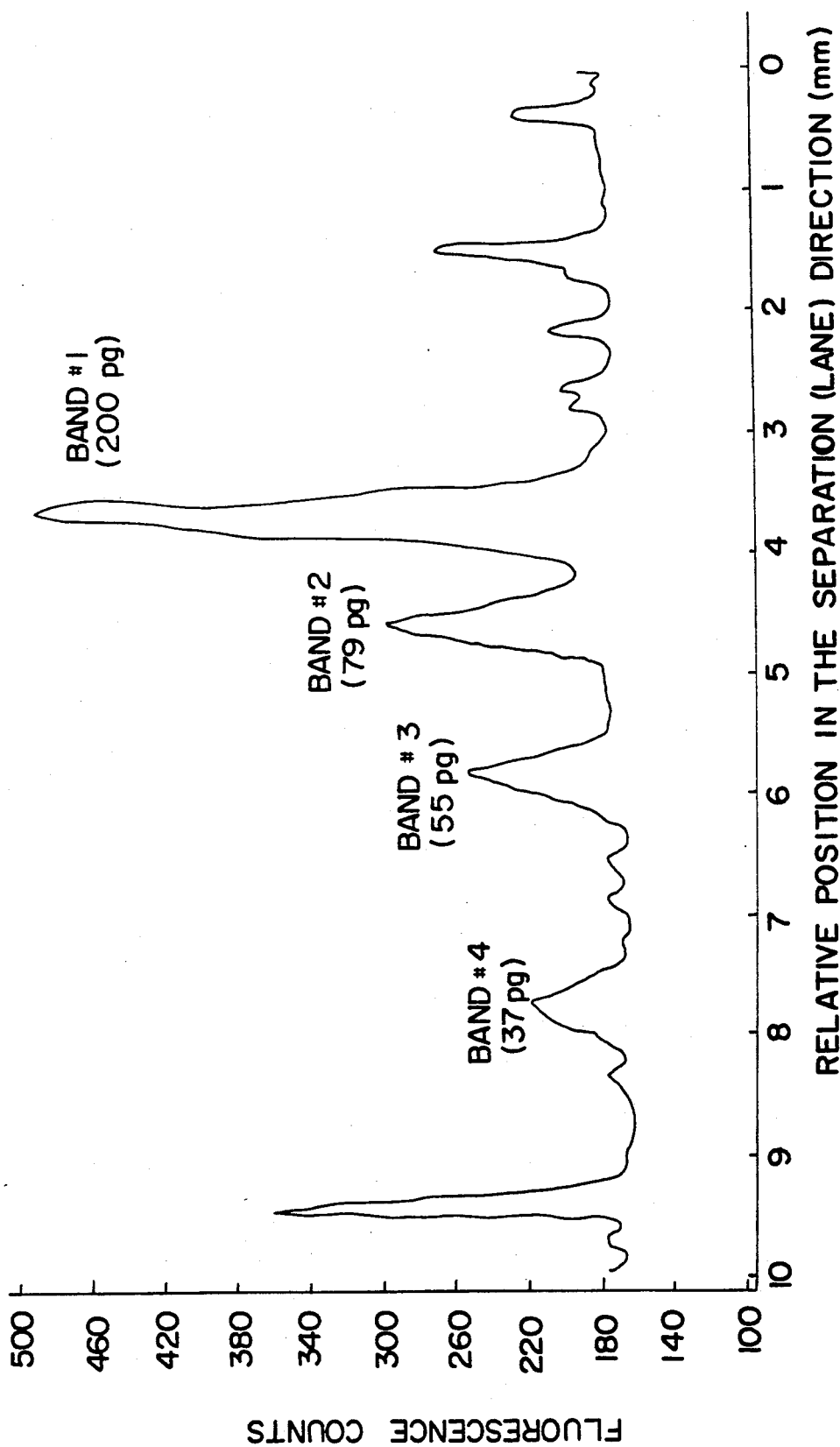
FIG. 10 shows an average of the scans shown in FIGS. 8 and 9.

Fourteen repeated scans of the 0.41 ng sample spaced 0.2 mm apart in the X-direction normal to the separation or lane direction were used to construct the three-dimensional plot shown in FIG. 8. Frequent noise spikes are present. (They do not appear round because the scale factor in the two directions differ.) Band #4 is not clearly detectable. The same data is shown in FIG. 9 as a contour plot. A simple average of the scans without baseline adjustment is shown in FIG. 10, excluding the two scans at the extreme edges of the lane where the amplitude of the sample peaks is reduced. Averaging is helpful in lowering the amplitude of the noise spikes, and band #4 is readily detectable.

EXAMPLE IV

Figure 11:
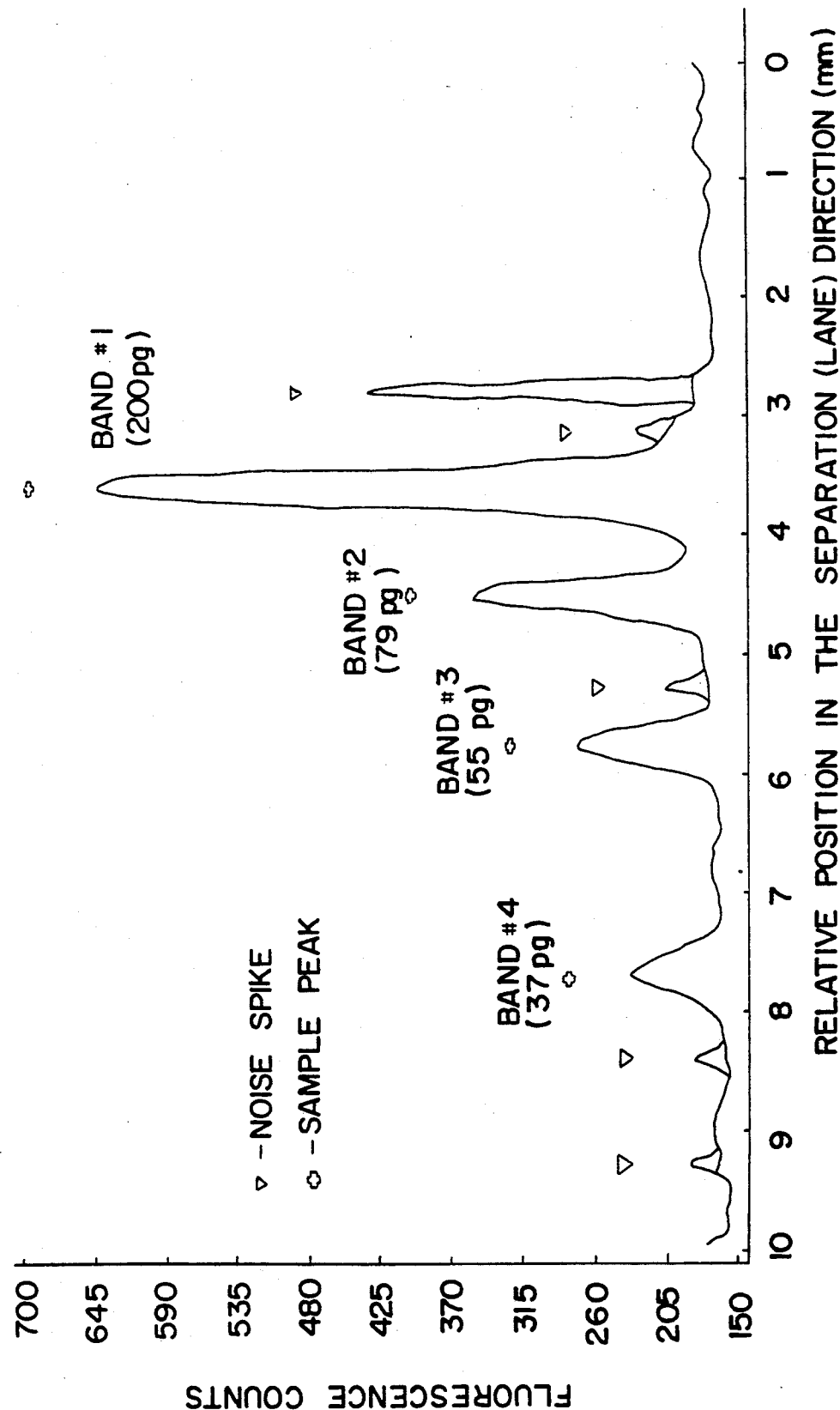
FIG. 11 illustrates the process of computer noise spike identification and truncation.
Figure 12:
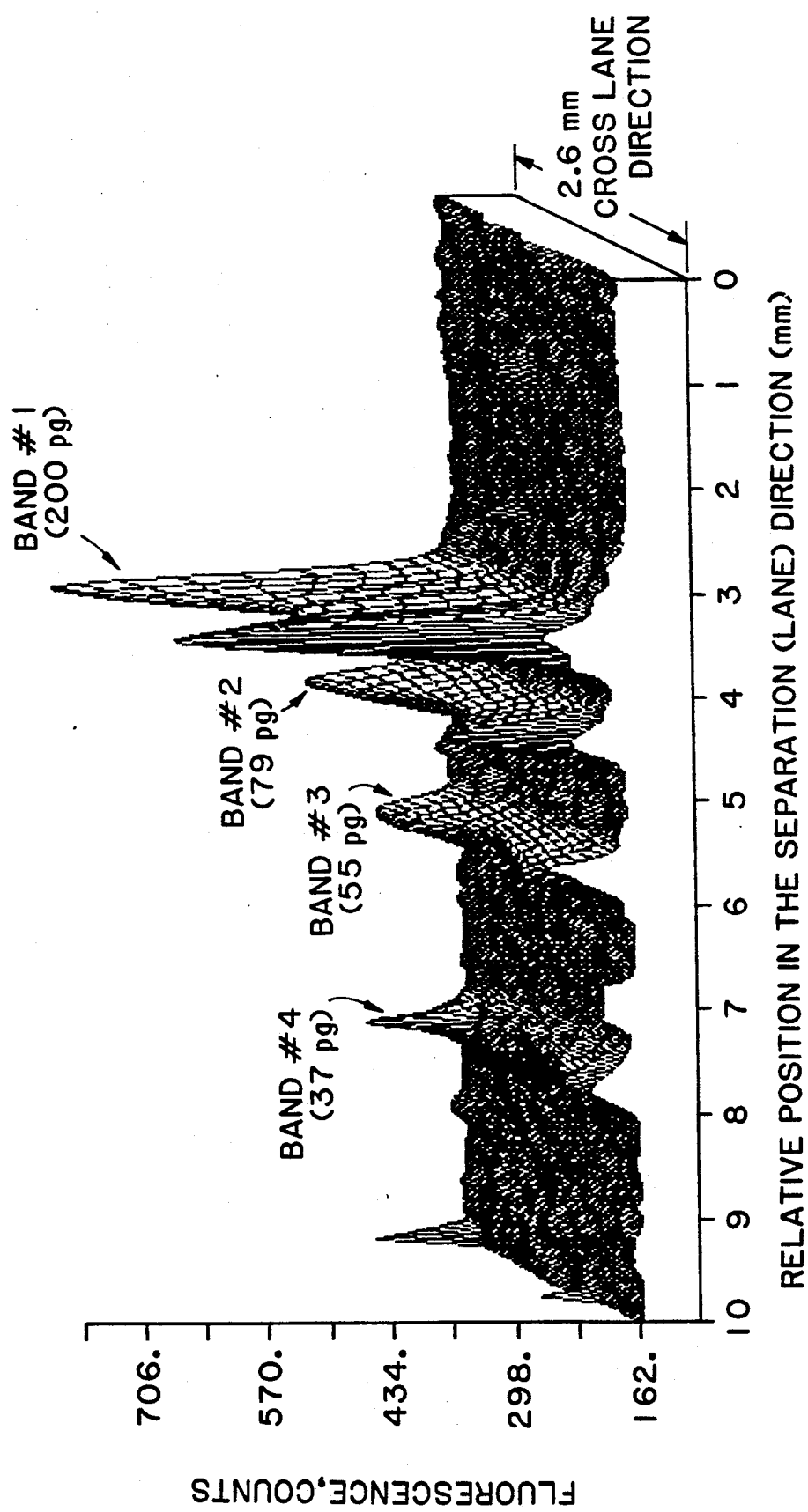
FIGS. 12–14 illustrate improvements in base line uniformity consequent from noise spike truncation.
Figure 13:
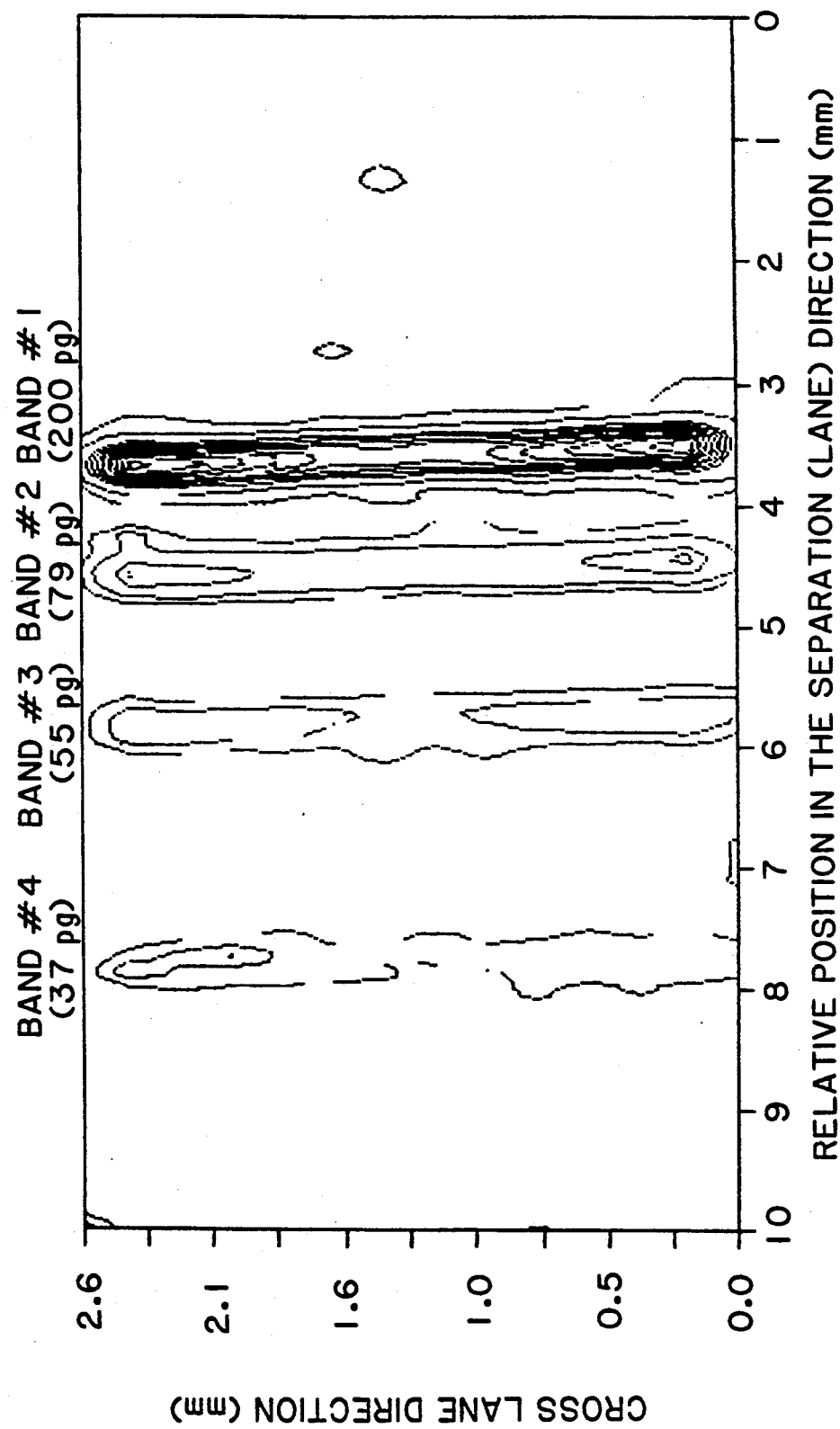
Figure 14:
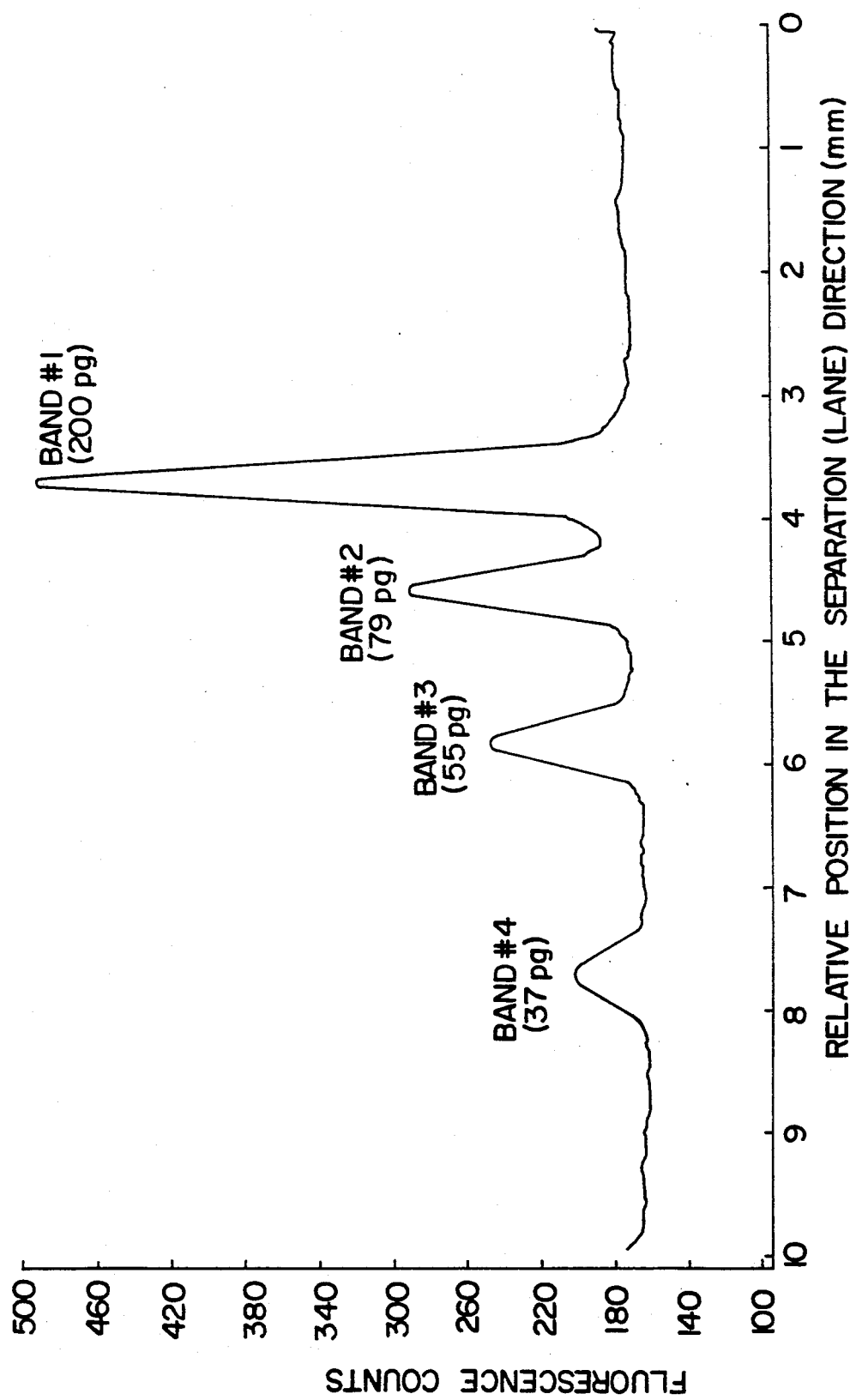

FIG. 11 illustrates the process of noise spike truncation performed by computer which was employed to remove this source of high frequency noise. Note that every noise spike is less than 0.2 mm wide and meets the FWHM test. The sample peaks are at least twice the width of the noise peaks. FIGS. 12, 13 and 14 show the considerable improvement in baseline uniformity which follows noise spike elimination.

EXAMPLE V

Figure 15:
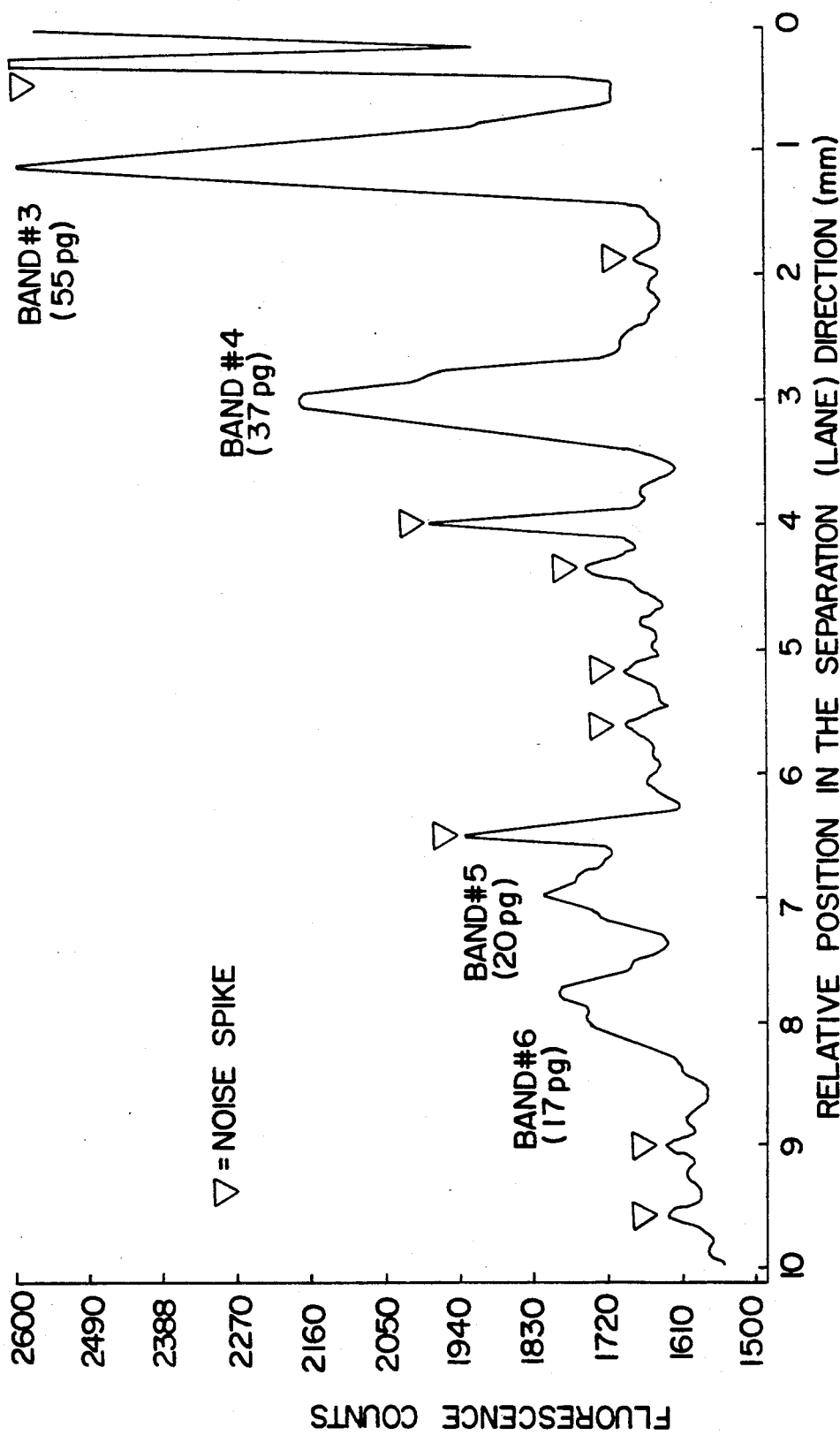
FIG. 15 shows one of 31 scans of bands #3–#6 spaced 0.1 mm apart of the 0.41 ng sample in the same lane after repositioning the gel a few mm in the Y-direction. The gain has been further increased so that band #3 is shown at full scale.
Figure 16:
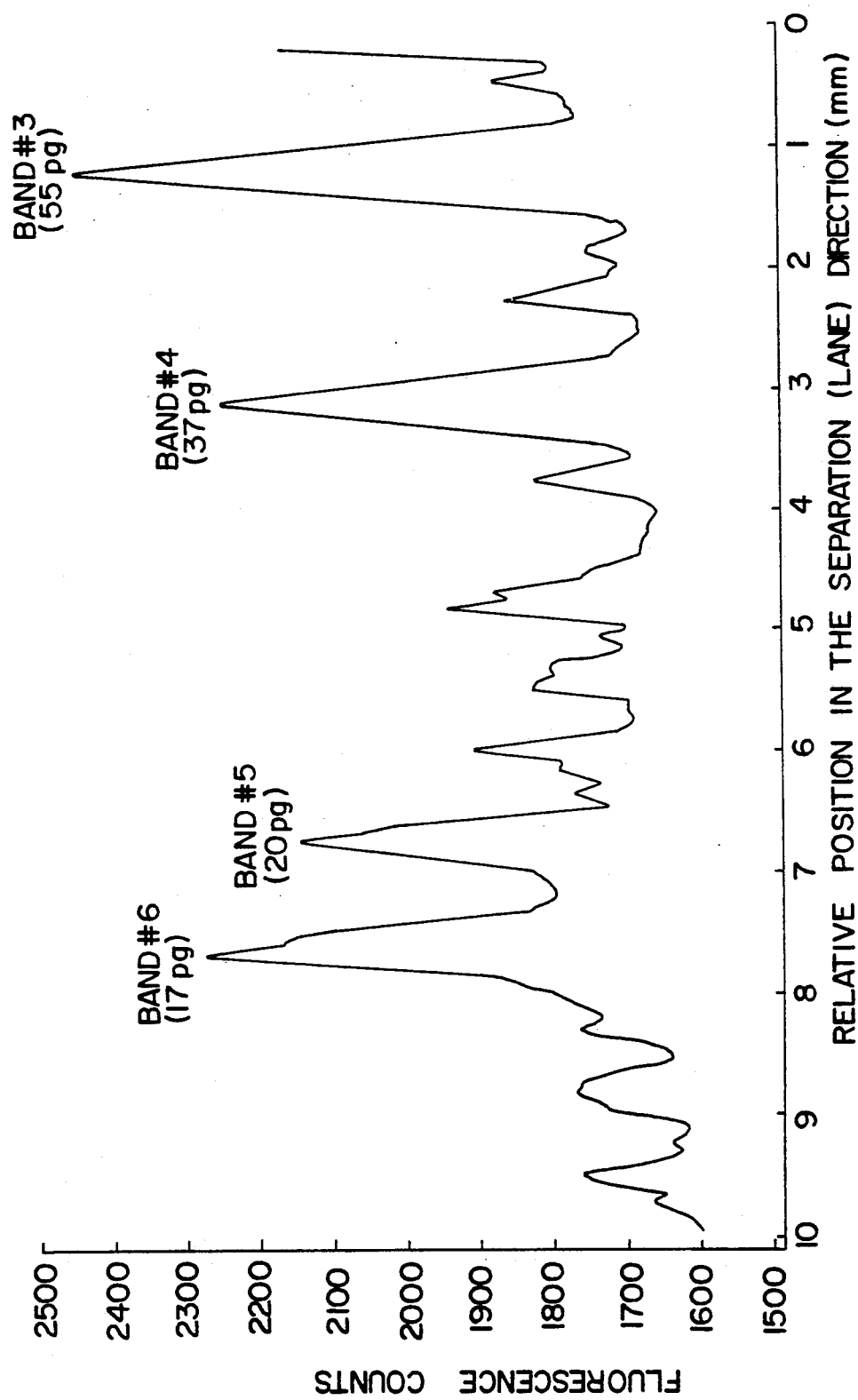
FIG. 16 shows an average of an inner subset of 25 adjacent scans taken within the 2.5 mm lane width without adjusting the individual scans up or downward.
Figure 17:
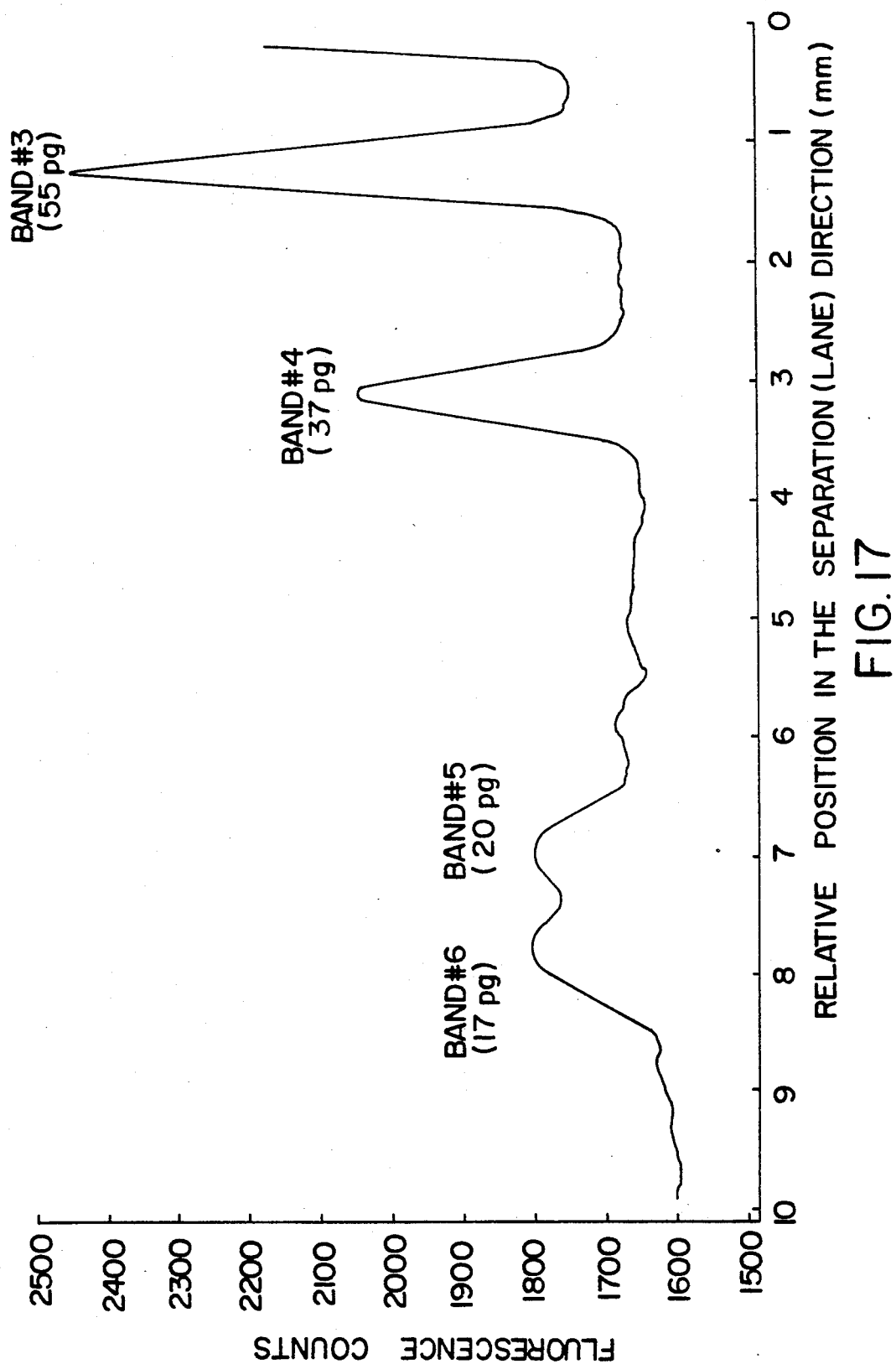
FIG. 17 shows the data of FIG. 16 after noise spike removal.

FIG. 15 shows one of the 31 scans of bands #3–#6 spaced 0.1 mm apart of the 0.41 ng sample described in Example I in the same lane after repositioning the gel a few mm in the Y-direction. The gain has been further increased so that band #3 is now shown at full scale. The noise spikes are even more evident. FIG. 16 shows an average of an inner subset of 25 adjacent scans taken within the 2.5 mm lane width, again without adjusting the individual scans up or downward. Note that the overlapping noise spikes which result after summation are now greater than the FWHM criterion in many instances and harder to differentiate from the sample peaks. Bands #5 and #6 are just detectable by their greater width. Averaging the 25 scans after noise spike removal leads to both a significant reduction in the remaining baseline variation and enhanced detectability of bands #5 and #6 as clearly evident in FIG. 17.

EXAMPLE VI

Figure 18:
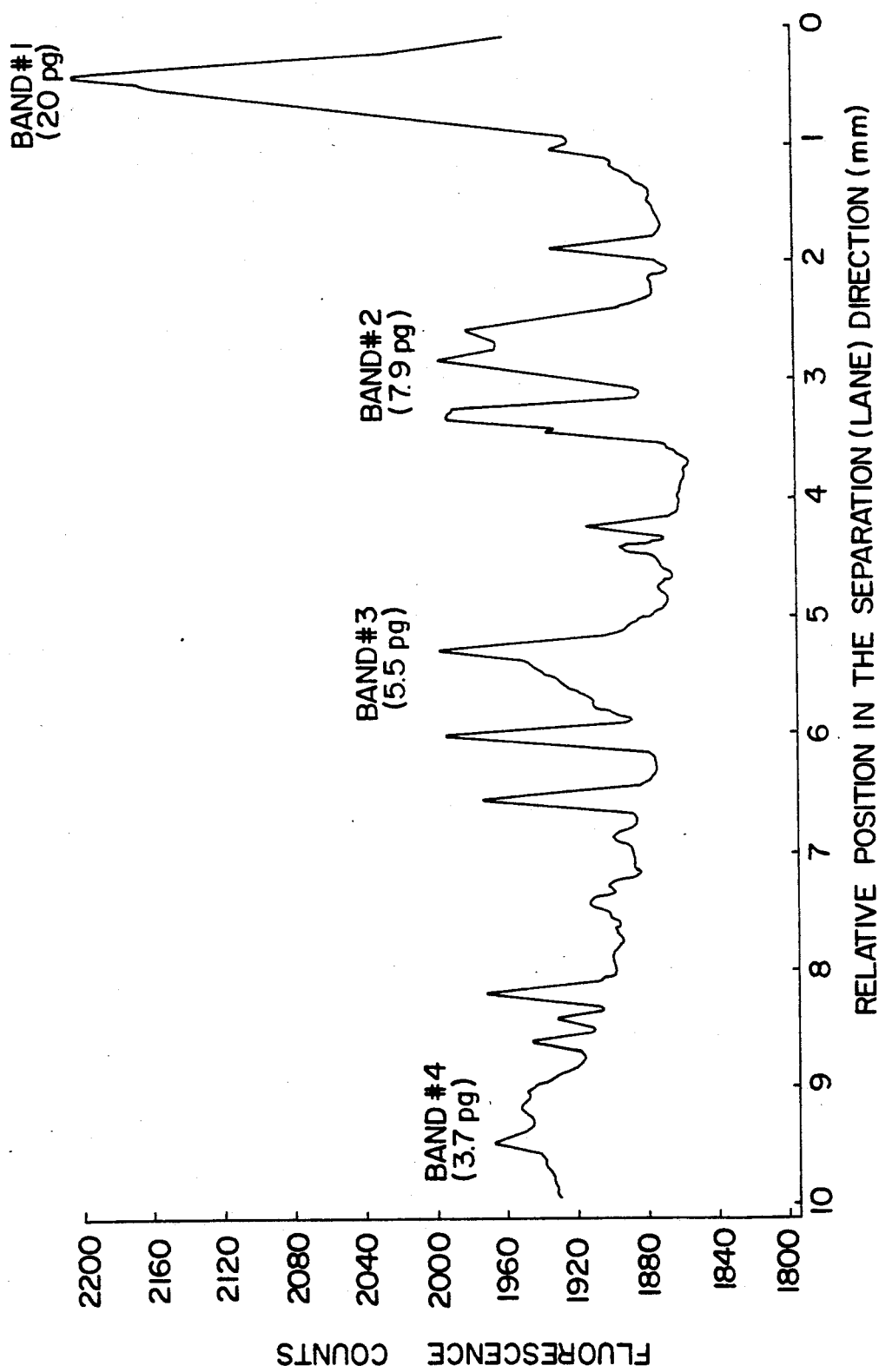
FIG. 18 shows an average of the inner subset of twenty-five adjacent scans of a 0.041 ng sample before noise spike removal.
Figure 19:
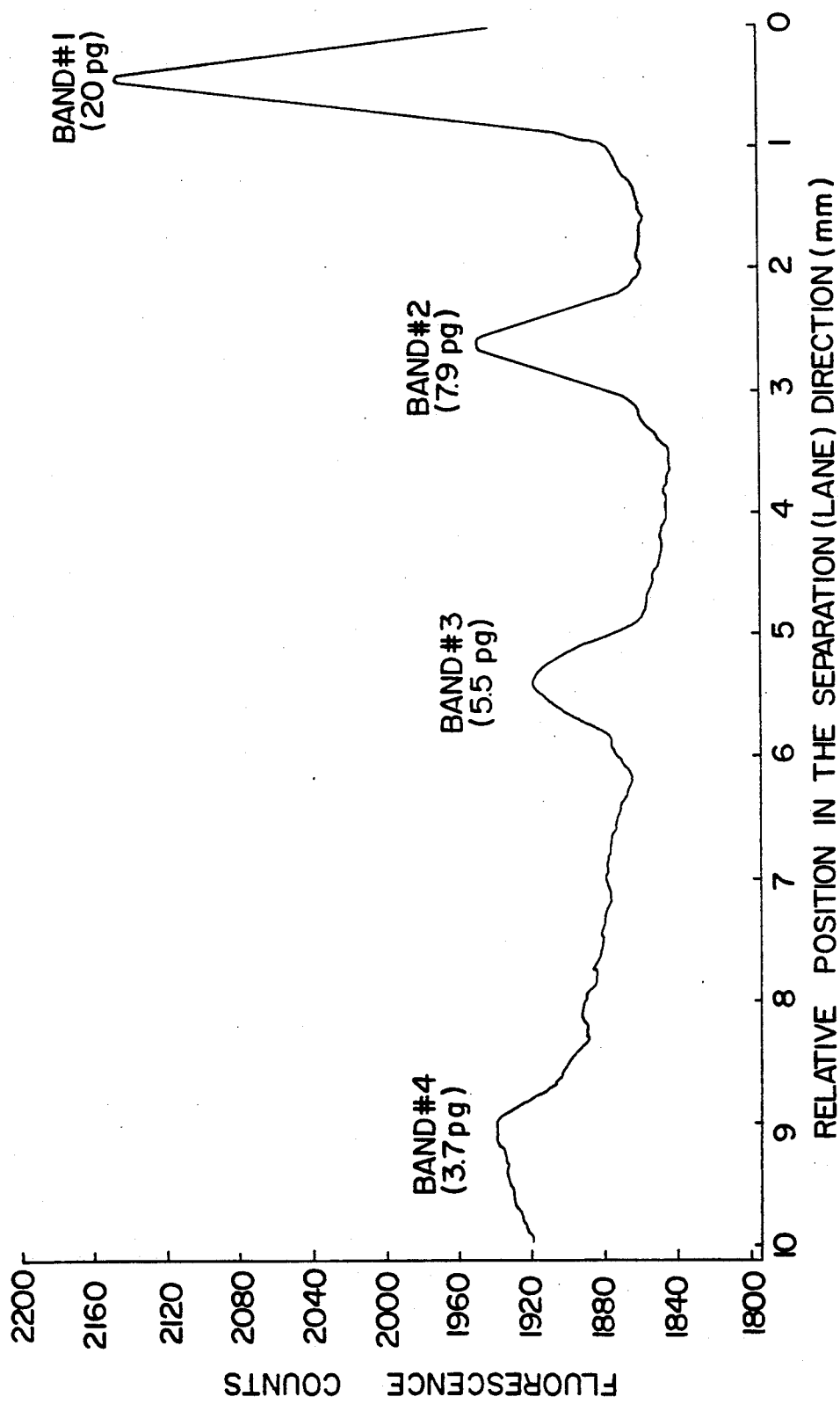
FIG. 19 shows data of FIG. 18 after noise spike removal.

FIG. 18 shows the average of 25 on-lane scans before noise spike removal for bands #1–#4 when the sample concentration is reduced further by 10× to 0.04 ng/band. Despite averaging only band #1 is clearly detectable. FIG. 19 shows that bands #2 and #3 are detectable after noise spike removal. Band #4 at 3.7 pg, is at the limit of detection. (The greater spacing between the bands shown in FIGS. 18 and 19 is primarily due to the longer separation time (50 minutes) than employed in Examples I–V.)

EXAMPLE VII

Figure 20:
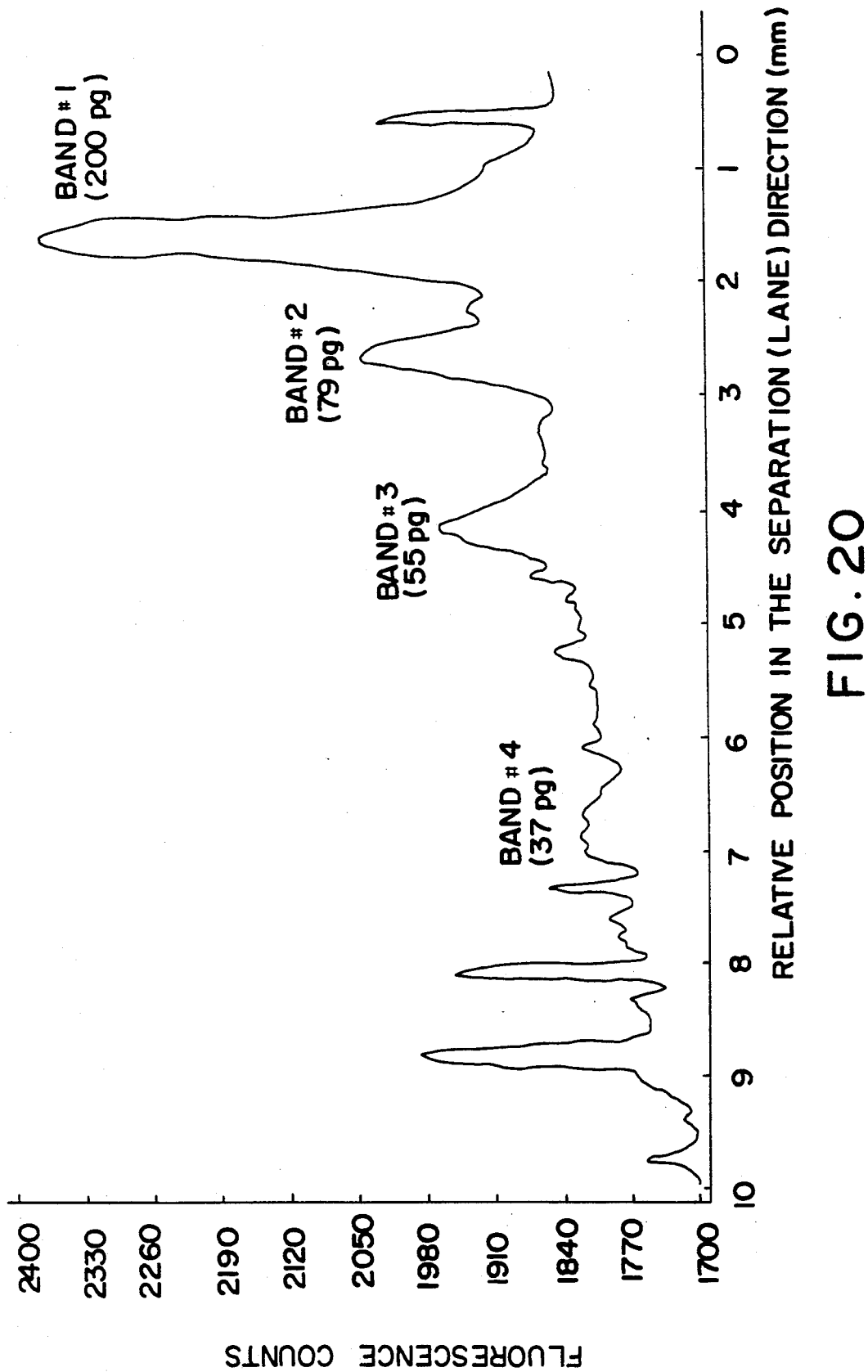
FIG. 20 shows the average of 12 scans 0.2 mm apart of a 0.4 ng sample, before noise spike removal, without using the means of this invention to improve background uniformity.
Figure 21:
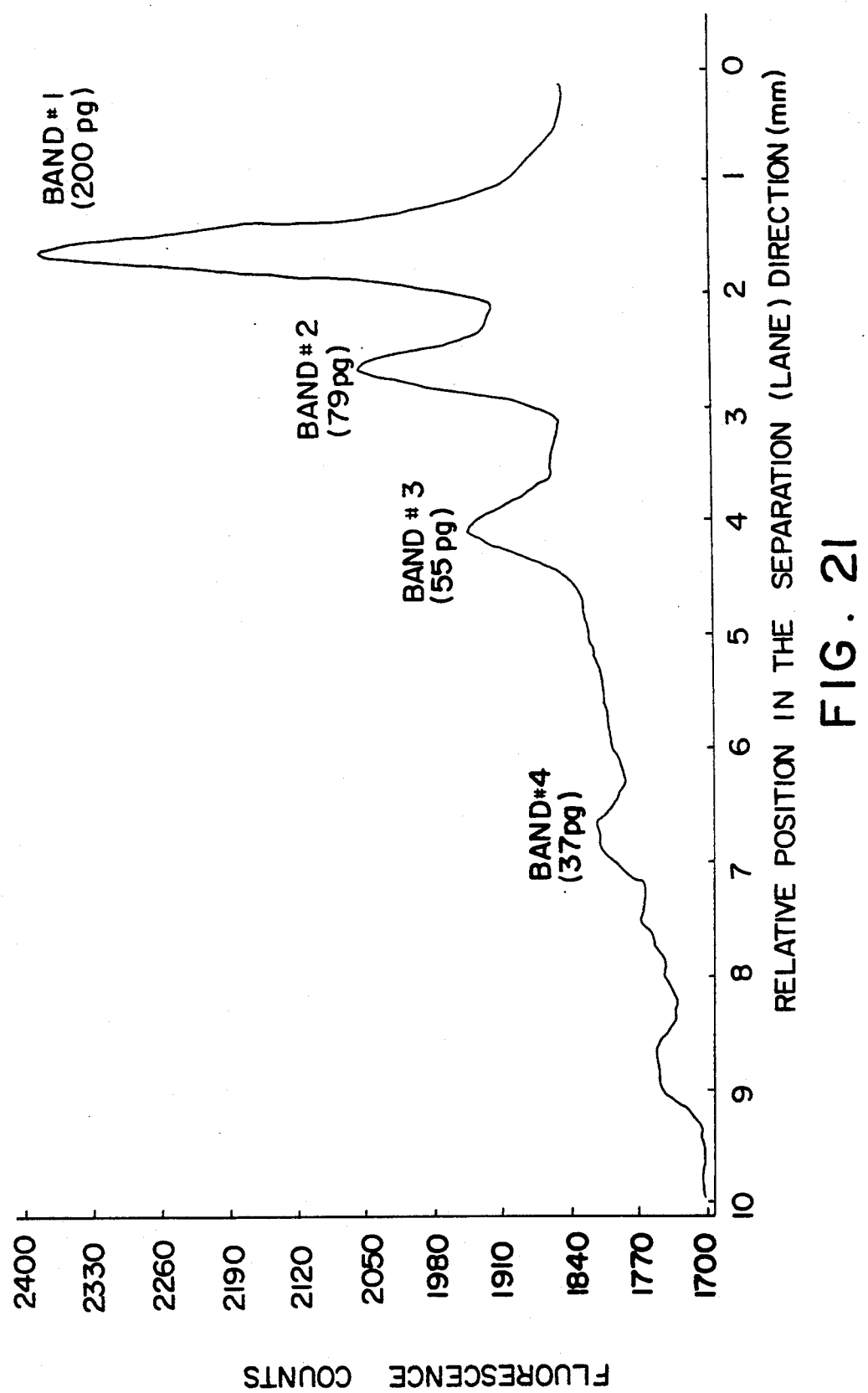
FIG. 21 shows data of FIG. 20 after noise spike removal.

As a basis of comparison, a gel was prepared without gel filtering using present, routine procedures. The gel was cast in an open plastic tray which was leveled by not preheated. It was covered while hardening to exclude gross dust contamination. A shorter, more commonly-employed destaining method was also used (21). The gel was destained for 30 minutes in 300 ml of 1× TBE buffer with occasional rocking. FIG. 20 shows an average of 12 scans of a 0.4 ng sample before noise spike removal. Despite the greater number of noise spikes (see Example VIII) bands #1–#3 are visible. Despite improvement with noise spike removal, FIG. 21 shows that band #4 at 37 pg cannot be differentiated from the apparent peak at the 9 mm scan position which is due to incomplete removal of several large noise spikes. The baseline is much less uniform than in Examples II through VI for the filtered gels as a consequence of both the greater number of noise peaks and the incomplete destaining.

EXAMPLE VIII

The size distribution of noise spikes is shown in Table 3 with and without gel filtering. In Example VII, little change occurs with the brief, 0.5 hour destaining. However, in a separately prepared, filtered gel, the 4.0 hour destaining with agitation leads to a several-fold decline. After destaining, the overall reduction in the number of noise spikes in each size range with the improved methods of the invention is 10× or greater in almost every size category compared to the unfiltered gel.

TABLE 3

Average Noise Spike Occurrence Rate Per 100 mm Scan Distance in Different Size Ranges

NUMBER OF NOISE SPIKES IN EACH SIZE RANGE. [COUNTS[1]]

| 0–10 | 10–20 | 20–30 | 30–40 | 40–50 | 50–100 | 100–200 | 200–500 | 500–1000 | 1000–2000 | 2000–4095 | >4095 |
|---|---|---|---|---|---|---|---|---|---|---|---|
| \multicolumn{12}{l}{Example VII: 3.0 mm thick gel cast in an open tray without gel filtering} | | | | | | | | | | | |
| \multicolumn{12}{l}{before destaining} | | | | | | | | | | | |
| 73. | 48. | 22. | 14. | 8.5 | 18. | 10. | 8.0 | 3.2 | 1.9 | 0.0 | 2.2 |
| \multicolumn{12}{l}{after 0.5 hours of destaining} | | | | | | | | | | | |
| 72. | 57. | 28. | 16. | 10. | 19. | 8.2 | 9.0 | 1.9 | 1.6 | 1.5 | 1.5 |
| \multicolumn{12}{l}{Separately prepared 3.0 mm thick gel cast between plates with gel filtering and cell purging} | | | | | | | | | | | |
| \multicolumn{12}{l}{before destaining} | | | | | | | | | | | |
| 24. | 10. | 2.6 | 1.8 | 0.8 | 2.5 | 2.6 | 1.5 | 0.4 | 0.2 | 0.0 | 0.0 |
| \multicolumn{12}{l}{after 4.0 hours of destaining[2]} | | | | | | | | | | | |
| 7.1 | 3.3 | 1.2 | 0.5 | 0.2 | 1.0 | 0.5 | 1.0 | 0.0 | 0.2 | 0.0 | 0.0 |

[1] 1.0 digital count = 250. uV at the A/D converter input. Average of 84 10 mm long scans 0.1 mm apart.
[2] Average of 42 10 mm scans.

EXAMPLE IX

The ability to detect small sample masses scanning through the casting plates is a necessary condition for satisfactory cassette operation. The procedures of Example I were followed with the following modifications in order to study this possibility. A 0.8 mm thick gel was cast between two low fluorescence quartz plates 6.0 mm thick and 50 mm square using a casting assembly closely similar to that shown in FIGS. 25 and 26. The separation was carried out in a home-made, vertical, Studier-type apparatus with upper and lower buffer reservoirs in contact with the exposed ends of the gel (21). A separate stacking gel was cast at one end of the completed plate assembly to provide sample loading wells. The sample volume was limited to 1.0 μl and Ficoll instead of glycerol was used in the loading buffer. The separation voltage was 50 V and the separation time was 30 minutes. Staining was accomplished by adding ethidium bromide (0.25 μg/ml) to the lower anode reservoir only. (The positively charged dye migrates through the gel toward the upper negative electrode.) Following the separation, the outer surfaces of the plates were cleaned and the sample scanned, allowing the laser beam to pass through both plates onto a black foam backstop located about 15 cm below on the optical benchtop.

Figure 22:
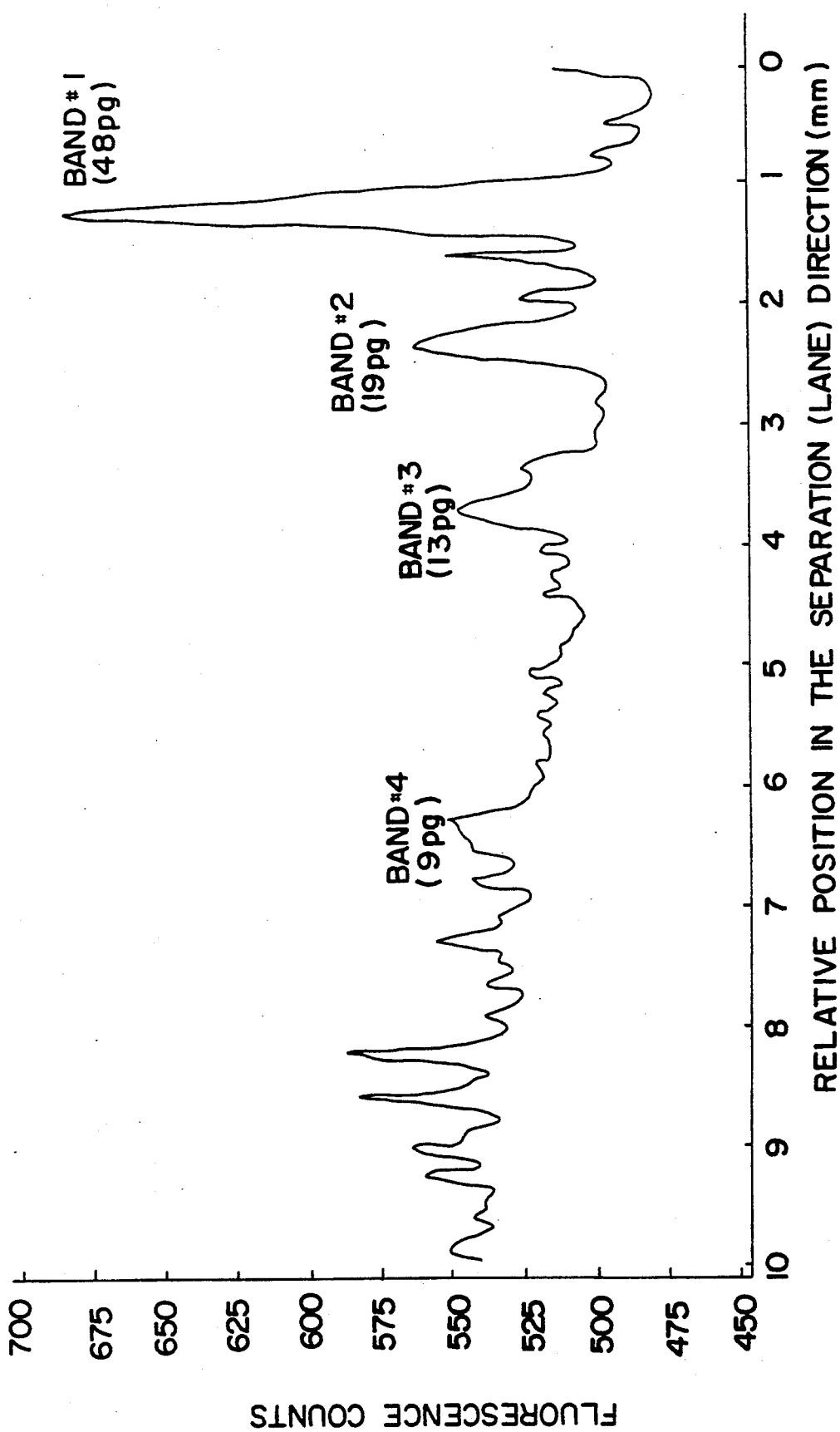
FIG. 22 shows an average of 23 scans of a 0.8 mm thick vertical gel cast and scanned between plates, 0.1 ng sample, before noise spike removal.
Figure 23:
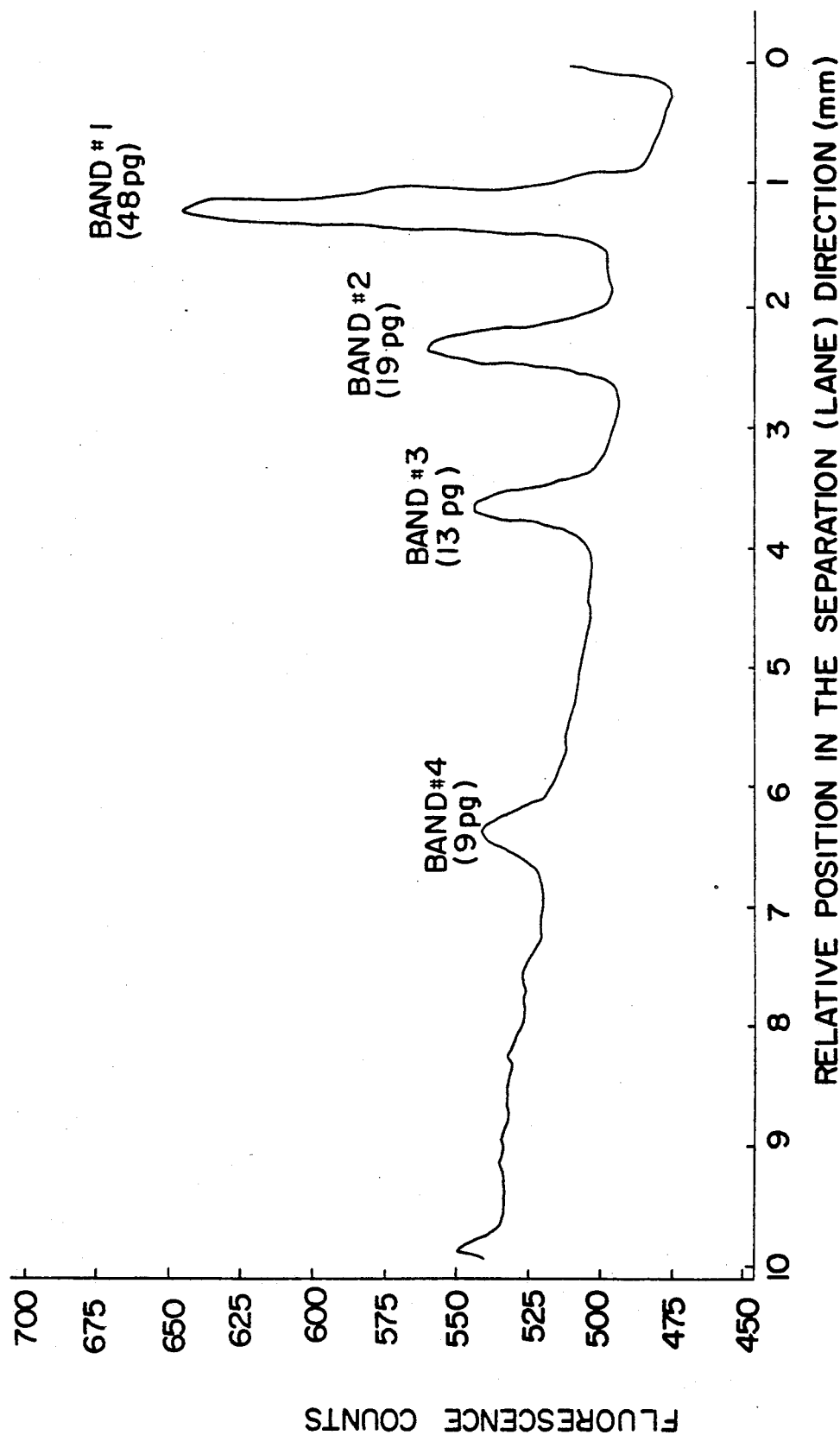
FIG. 23 shows data of FIG. 22 after noise spike removal.

FIGS. 22 and 23 show the average of 22 scans of a 0.1 ng sample, bands #1–#4, before and after noise spike removal. The estimated detection limit is 4. pg/band. (The slope in this background is due to the dye concentration gradient associated with its method of introduction.) The data demonstrates that good detection is achievable in a thin gel cast and maintained between transparent plates in the absence of destaining.

EXAMPLE X

Figure 24:
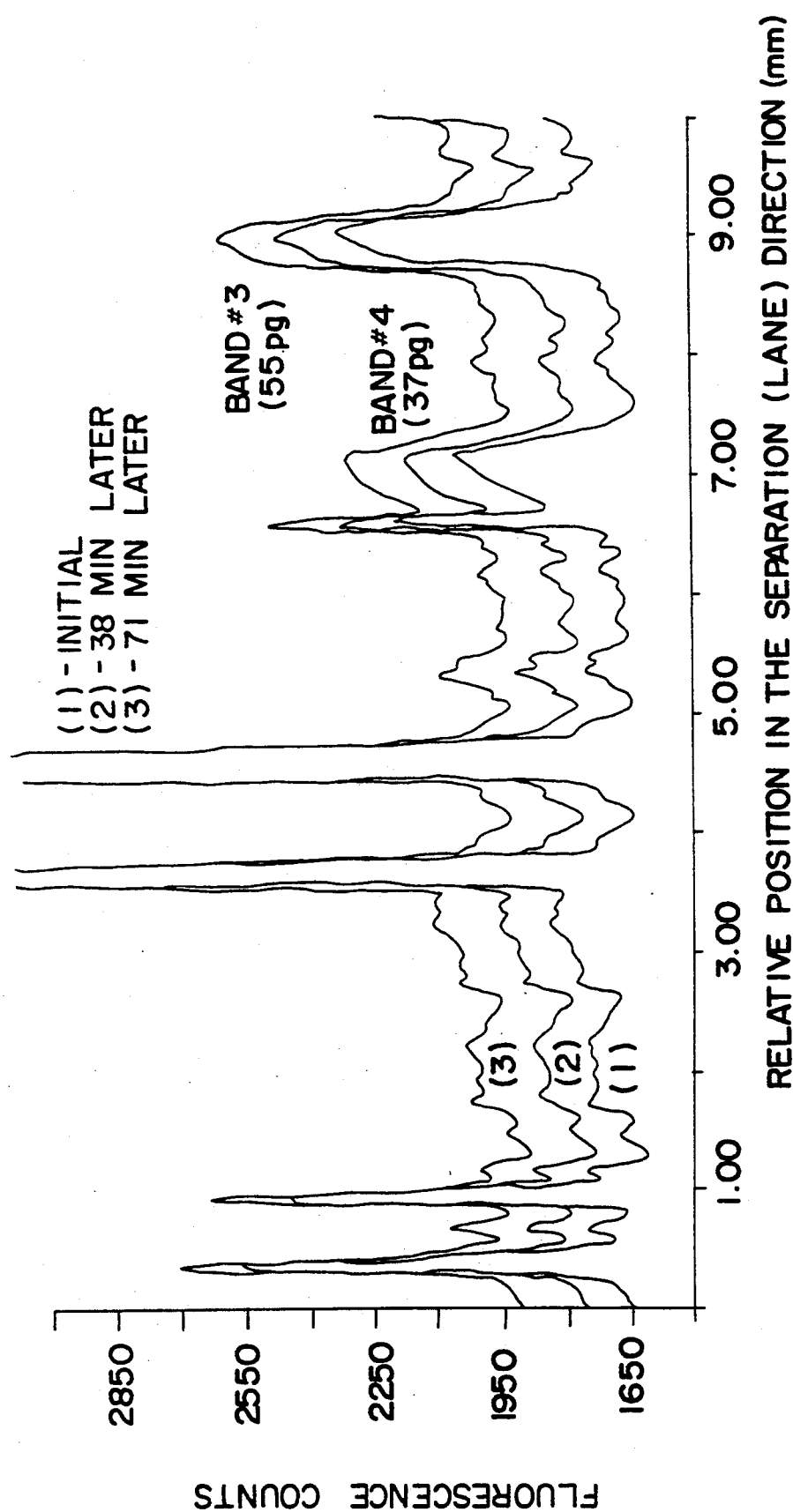
FIG. 24 is a comparison of three repeated scans over a time period exceeding one hour.

FIG. 24 demonstrates the high degree of scan repeatability which can be achieved by the instrument illustrated by FIG. 4 over a time interval exceeding one hour. The baseline variability is highly reproducible. This behavior demonstrates long term stability of both the measurement system and the gel.

Alternative Scanning Modes of Operation

Accurate noise spike elimination requires high resolution scanning a minimum of 300 to 500 data points per cm. The specific instrument shown in FIG. 4 provides the required high resolution at a relatively slow scanning rate, for example, at 0.5 mm/second, 5000 seconds are required to scan a gel lane 50 mm long by 5.0 mm wide with complete area coverage using a 0.1 mm diameter spot. Substitution of a laser of 5× higher power, for example, a commercially available 543.5 nm HeNe 1.5 mW instrument, permits increasing the scan speed by 25× to 12.5 mm/second with no loss in signal-to-noise. The scan time would then be reduced from 5000 seconds to 200 seconds. Furthermore, the method of the invention is directly extendible to much faster scanning speeds without impairing analytical performance by using a higher power laser and one of several rapid, laser beam deflection techniques (3). Alternatively, a low power argon-ion laser operating at 514.5 nm with a power output of 30 mW can be used to scan rapidly a 100 cm[2] gel area in 40 seconds at high resolution with a 0.1 mm diameter laser spot.

Faster scanning with somewhat lower resolution can be achieved with the instrument of FIG. 4 by reimaging the laser spot as a rectangle in a known manner. For example, a rectangle 0.1 mm in the separation (Y direction) by 2.0 mm in the opposite X-direction, i.e., slightly less than the lane width, is appropriate. A single scan down the center of a lane at 12.5 mm/second is sufficient to survey rapidly a 50 mm long lane in 4 seconds vs the 200 seconds required by the high resolution method. The peak fluorescence signal and band resolution would be unchanged (product of irradiance and sample illuminated area remains constant) for an ideal gel with a one-dimensional distribution of DNA varying in the Y-direction only. However, skewed or distorted bands may impair the resolution of closely spaced bands. The ability to quantitate accurately the mass of DNA may also be less since the net sample fluorescence cannot be determined with as much accuracy. (For example, the fluorescent signal is now dependent upon the details of the laser power variation within the rectangular spot.) Nevertheless, this alternative mode of operation provides a rapid, useful, initial survey scan which can be followed by slower, high resolution scanning over smaller selected regions of the gel.

SUMMARY

This invention, in its various aspects, is attended by many advantages as compared with the prior art.

1. Lower Detection Limits—The analytical performance is superior to the methods presently employed for directly detecting and recording fluorescence from an ethidium bromide stained gel. An important improvement in performance is that much lower detection limits can be achieved than by either (1) visual observation, (2) photography, or (3) electronic imaging using a UV transilluminator as the excitation source. The present detection limit with these methods is 0.3 to 0.5 ng/band (300 to 500 pg/band), while this instrument will measure 1.0 to 5.0 pg/band; at least a factor of 100× improvement.

2. Extended Dynamic Range—The ability to measure 1.0–5.0 pg/band imposes an increased dynamic range requirement for the detection system if very weak and very strong bands are to be measured on the same gel. The upper limit for sample concentration at which point the fluorescence is no longer proportional to the stained DNA mass is estimated to be between 100 and 500 ng/band. The dynamic range expressed as the ratio of maximum to minimum signals is, therefore, at least $1 \times 10^5$. The linear response of a silicon photodiode or photomultiplier detector which would be used in these single channel instruments can easily encompass this range. In contrast, photography in particular and even electronic imaging would require multiple exposures, even if capable of requisite sensitivity.

3. More Accurate Nucleic Acid Mass Quantitation—More accurate quantitation of the mass of nucleic acid in each band is a consequence of the improved instrumental approach which uses (1) laser excitation with a small spot size and a low divergence beam waist, together with nearly normal incidence to achieve high resolution and low field distortion; (2) a very low noise, low drift fluorescence excitation and detection system; (3) visible wavelength excitation, in contrast to shorter wavelength UV excitation, which leads to (a) less downward signal drift caused by dye bleaching, and (b) less beam attenuation caused by scattering and absorption as the beam passes through the gel; (4) a stained gel with much more uniform background fluorescence; and (5) an improved background correction technique made possible by the improvements in gel uniformity; (6) a cassette and thin gel.

4. Reduced Photodamage—Visible excitation (lower photon energy) used in a transient, scanning mode versus continuous UV exposure occurring with a transilluminator almost certainly reduces the rate of photoinduced damage to the nucleic acid. This reduction may prove important for preparative separations where a large DNA fragment is used in a subsequent cloning step.

5. Improved Automation—Measurements made from the gel can be automated with less operator intervention. The present labor intensive step of photographing the stained gel on a UV transilluminator table is eliminated. Use of the gel cassette further eliminates gel preparation, staining and destaining, and careful positioning of the sample within the scanning instrument.

REFERENCES

1. J. B. Le Pecq, *Meth. Biochem. Anal.* 20:41 (1971)
2. A. Prunell, et al. *Anal. Biochem.* 78:57 (1977)
3. S. A. Myers, SBIR Phase I Final Report, U.S. Department of Energy, Proposal Number 5832-87-I, DOE Contract No. DE-AC01-87ER80471 (Feb. 2, 1988)
4. J. C. Sutherland, et al., *Anal. Biochem.* 163:446 (1987)
5. S. Forsblom, et al., *Nucleic Acids Res.* 3:3255 (1976)
6. W. Ansorge, et al., *Nucleic Acids Res.* 15:4593 (1987)
7. L. R. Middendorf, et al., *Amer. Biotech. Lab.* 6(6):14 (1988)
8. L. M. Smith, et al., *Nature* 321:674 (1986)
9. J. M. Prober, et al., *Science* 238:336 (1987)
10. W. Ansorge, et al., FRG Patent No. DE 3618605 A1 (1987)
11. L. R. Middendorf and J. A. Brumbaugh, U.S. Pat. No. 4,729,947 (Mar. 3, 1988)
12. B. M. Sutherland, et al., *Annals of the New York Academy of Sciences* 453:73 (1985)
13. S. E. Freeman, et al., *Anal. Biochem.* 158:119 (1986)
14. J. A. Matthews and L. J. Kricka, *Anal. Biochem.* 169:1 (1988)
15. C. F. Brunk, and L. Simpson, *Anal. Biochem.* 82:455 (1977)
16. G. Varani, et al. *J. Chem. Soc., Faraday Trans.* 1 83:1609 (1987)
17. T. Maniatis, et al., *Molecular Cloning. A Laboratory Manual,* Cold Spring Harbor Laboratory, Cold Spring Harbor, N.Y. (1982)
18. A. T. Andrews, *Electrophoresis: Theory, Techniques, and Biochemical and Clinical Applications,* 2d Ed. (Oxford University Press, New York 1986)
19. Isolab Inc., Akron, Ohio, Bulletin "Electrophoresis Products Featuring Gels-To-Go" (Revised Feb. 15, 1988)
20. G. H. J. Turre, et al., U.S. Pat. No. 4,415,418 (Nov. 15, 1983)
21. D. Rickwood and B. D. Hames, *Gel Electrophoresis of Nucleic Acids; a Practical Approach,* 1st ed. (IRL Press Ltd., Oxford 1982)

I claim:

1. A system for analyzing fluorophore stained, electrophoretically separated nucleic acid fragments present in at least one band in at least one gel sample which comprises the following elements:
   (i) a constant output laser;
   (ii) narrow bandpass filter means for blocking incoherent light from the laser beam;
   (iii) means for controlling the laser beam to provide a preselected beam waist and spot diameter;
   (iv) means for directing said beam having said preselected spot diameter on said gel sample at about a minimum incidence angle sufficient to suppress interference fringing;
   (v) means for exposing said at least one band in said gel sample to said laser beam spot;
   (vi) lens means for collecting the fluorescent signal generated by the passage of said at least one nucleic acid fragment containing band in said gel through said laser beam spot, for passing said collected signal through filters for blocking light at the excitation wavelength and through an imaging lens onto a detector to measure the intensity of fluorescence from said at least one band,
   said lens being shielded from ambient and stray light interference; and
   (vii) computer means for processing the fluorescence intensity data, said computer means truncating noise spikes at the base, when said noise spikes have a full width at half maximum in a plot of fluorescent intensity versus separation direction that is less than the width of a peak for a nucleic acid band in said same plot.

2. A system as defined in claim 1 in which the laser element (i) produces a constant output at a wavelength of from about 250 nm to about 575 nm.

3. A system as defined in claim 1 in which the laser element (i) produces a constant output at a wavelength of from about 500 nm to about 550 nm.

4. A system as defined by claim 1, 2, or 3 in which the element (iii) provides a spot diameter comprising means to control said spot diameter to about as small as 0.005 mm.

5. A system as defined by claim 1, 2 or 3 in which said sample is contained in a closed cell and in which said element (iv) includes means for directing said beam on said gel at substantially normal incidence.

6. A system as defined by claim 1, 2 or 3 in which said sample is contained in a gel cassette and in which said element (iv) includes means for directing said laser beam on said sample at the minimum incidence angle sufficient to suppress interference fringing.

7. A system for determining the mass of fluorophore stained, electrophoretically separated nucleic acid fragments in at least one band in at least one gel sample, said system being useful to measure mass down to from about 1.0 to about 5.0 picograms of nucleic acid per band, said system comprising the following elements:
   (i) a visible light constant output laser;
   (ii) narrow band pass filter means for blocking incoherent light from the laser beam;
   (iii) a sample gel cassette, the gel in said cassette being less than 1 mm thickness, being positioned in contact with and between smooth parallel surfaces of the cassette and said gel being substantially free of particulates of size greater than about 0.20 microns,
   (iv) means for directing said laser beam at a preselected spot diameter and at an incidence of from about 0 to about 10 degrees on said gel in said cassette;
   (v) means for passing said gel sample in said cassette through said laser beam spot;
   (vi) lens means for collecting the fluorescent signal generated by the passage of said at least one nucleic acid fragment containing band in said gel through said laser beam spot, for passing said collected signal through filters for blocking light at the excitation wavelength and through an imaging lens onto a detector to measure the intensity of fluorescence from said at least one band, said lens means being shielded from ambient and stray light interference; and
   (viii) computer means for processing the fluorescence intensity data, said computer means truncating noise spikes at the base, when said noise spikes have a full width at half maximum in a plot of fluorescent intensity versus separation direction that is less than the width of a peak for a nucleic acid band on said same plot.

8. A system as defined by claim 7 in which the laser element (i) provides a constant output at a wavelength of from about 500 nm to about 550 nm.

9. A system as defined by claim 7 in which the laser beam focusing element (iv) includes means for providing a preselected spot diameter at the minimum angle sufficient to suppress interference fringing.

10. A system as defined by claims 7, 8 or 9 in which said sample gel in said sample gel cassette element (iii) includes a plurality of samples each containing at least one band containing nucleic acid fragments whereby the mass of the nucleic acid fragments in each of said bands may be sequentially determined.

11. A method for determining the mass of fluorophore stained nucleic acid fragments in at least one band in at least one gel sample which comprises the following steps:
   (i) exposing said gel sample including said at least one nucleic acid fragment band to a focused, visible light, constant output laser beam
      said beam being substantially free of incoherent light and having a spot diameter that can be as small as about 0.005 mm and being directed on said band at an incidence of not more than about ten degrees;
   (ii) collecting the fluorescent signal generated by step (i);
   (iii) measuring the intensity of the fluorescence in the collected signal under conditions such that said signal is free of light at the excitation wavelength;
   (iv) processing the fluorescence intensity data from step (iii) to determining the mass of the nucleic acid fragments in said at least one band, said processing step including truncation at the base of noise spikes having a full width at half maximum in a plot of fluorescent intensity versus separation direction that is less than the width of the peak for a nucleic acid band of said same plot.

12. A method as defined by claim 11 in which said gel sample includes fluorophore stained nucleic acid fragments in a plurality of bands and in which the mass of the nucleic acid in each of said bands is determined sequentially.

13. A method as defined by claim 11 in which said constant output laser beam has a wavelength of from about 500 nm to about 550 nm.

14. A method as defined by claim 11, 12 or 13 in which said gel sample is a slab gel sample in a closed cell and in which said laser beam is directed on said sample at about the minimum incidence angle sufficient to suppress interference fringing.

15. A method as defined by claim 11, 12 or 13 in which said gel sample is a slab gel in a closed cell.

16. A method as defined by claim 11, 12 or 13 in which said gel sample is in a gel cassette in which the gel is less than 1 mm thick and in which said laser beam is directed on said gel at about the minimum incidence angle sufficient to suppress interference fringing.

17. A method useful to determining the presence of from about 1.0 to about 5.0 picograms a nucleic acid in an electrophoretically separated band of fluorphore stained nucleic acid in a gel which comprises the steps of
   (i) providing a gel cassette including a slab gel less than 1.0 mm in thickness, said gel substantially free of particulates larger than about 0.20 microns and positioned in contact with and between the parallel surfaces of upper and lower plates
      said gel including at least one electrophoretically separated band containing fluorophore stained nucleic acid fragments;
   (ii) exposing said gel including said at least one band to a focused, visible light constant output laser beam
      said beam being substantially free of incoherent light and having a spot diameter that can be as small as about 0.005 mm and being directed on said gel at about the minimum incidence angle to suppress interference fringing;
   (iii) passing said at least one band through said laser beam;
   (iv) collecting the fluorescent signal generated in step (iii);
   (v) measuring the intensity of the fluorescence in the collected signal under conditions such that said signal is free of light at the excitation wavelength;
   (vi) processing the fluorescence intensity data from step (iv) to determine the mass of the nucleic acid fragments in said at least one band, said processing step including truncation at the base of noise spikes having a full width at half maximum in a plot of fluorescent intensity versus separation direction that is less than the width of the peak for a nucleic acid band on said same plot.

18. A method as defined by claim 17 in which the gel of said sample is an agarose gel or a polyacrylamide gel.

19. A method as defined by claim 17 in which the fluorophore is ethidium bromide.

20. A method as defined by claim 17, 18 or 19 in which the particle content of said gel in said cassette and the number of particles in said gel is such that the noise spikes observed in a plot of the data from step (vi) have a full width at half maximum which is less than the width of the peak for a separated nucleic acid band in said gel.

* * * * *